United States Patent [19]
Nixon et al.

[11] Patent Number: 5,629,165
[45] Date of Patent: May 13, 1997

[54] NEURAL CALCIUM-ACTIVATED NEUTRAL PROTEINASE INHIBITORS

[75] Inventors: Ralph A. Nixon, Arlington; Kiyoshi H. Takeuchi, Newton, both of Mass.

[73] Assignee: The McLean Hospital Corporation, Belmont, Mass.

[21] Appl. No.: 202,023

[22] Filed: Feb. 25, 1994

Related U.S. Application Data

[60] Division of Ser. No. 735,611, Jul. 25, 1991, Pat. No. 5,340,922, which is a continuation-in-part of Ser. No. 356,458, May 25, 1989, abandoned, which is a continuation-in-part of Ser. No. 200,141, May 31, 1988, abandoned.

[51] Int. Cl.$^6$ ............................................. G01N 33/567
[52] U.S. Cl. .................... 435/7.21; 435/40.5; 530/388.2; 530/389.1
[58] Field of Search ........................... 435/7.21, 40.5; 530/389, 388.2, 389.1

[56] References Cited

U.S. PATENT DOCUMENTS 5,189,144  2/1993  Asada et al. ............................. 530/324

OTHER PUBLICATIONS

Minkovitz et al J. Neurochem 48(Suppl) S149, 1987.

Asada et al., "cDNA Cloning of Human Calpastatin: Sequence Homology among Human, Pig, and Rabbit Calpastatins", *J. Enzyme Inhibition* 3:49–56 (1989).

Copy of International Search Report for corresponding international application PCT/US92/06192.

Dyrks et al., "Identification, transmembrane orientation and biogenesis of the amyloid A4 precursor of Alzheimer's disease", *EMBO J.* 7:949–957 (1988).

Emori et al., "Endogenous inhibitor for calcium–dependent cysteine protease contains four internal repeats that could be responsible for its multiple reactive sites", *Proc. Natl. Acad. Sci. USA* 84:3590–3594 (Jun. 1987).

Imajoh & Suzuki, "Reversible interaction between $Ca^{2+}$-activated neutral protease (CANP) and its endogenous inhibitor", *FEBS* 187:47–50 (Jul. 1985).

Ishiura et al., "Purification of an Endogenous 68000–Dalton Inhibitor of $Ca^{2+}$-activated neutral protease from chicken skeletal muscle", *Biochim. et Biophys. Acta* 701:216–223 (1982).

Kimball, J., "Introduction to Immunology", third edition, pp. 20 and 67, published by Macmillan, New York (1990).

Lauffart et al., "Comparison of $Ca^{2+}$-activated proteinase enzyme and inhibitor levels in cerebral cortex from normal and Alzheimer disease cases", *Biochem. Soc. Trans., 627th Meeting, Nottingham*, 17:206–207 (1989).

Minkovitz et al., "Characterization of Two Endogenous Calpain Inhibitors from Human Brain", *J. Neurochem.* 48:S149:C (1987).

Myers et al., "The human mid-size neurofilament subunit: a repeated protein sequence and the relationship of its gene to the intermediate filament gene family", *EMBO J.* 6:1617–1626 (1987).

Nakamura et al., "Purification and Characterization of an Inhibitor of Calcium–Activated Neutral Protease from Rabbit Skeletal Muscle: Purification of 50,000–Dalton Inhibitor", *J. Biochem.* 96:1399–1407 (1984).

Nakamura et al., "Purification and Characterization of 210,000–Dalton Inhibitor of Calcium–Activated Neutral Protease from Rabbit Skeletal Muscle and Its Relation to 50,000–Dalton Inhibitor", *J. Biochem.* 98:757–765 (1985).

Nixon, R., "Proteolysis of Neurofilaments", in: Neurofilaments (Marotta, C.A., ed.), pp. 117–154, Univ. Minnesota Press, Minneapolis, Minnesota (1983).

Nixon et al., "Multiple Calcium–Activated Neutral Proteinases (CANP) in Mouse Retinal Ganglion Cell Neurons: Specificities for Endogenous Neuronal Substrates and Comparison to Purified Brain CANP", *J. Neurosc.* 6:1252–1263 (May 1986).

Nixon et al., "Human Brain Proteolysis in Aging and Alzheimer's Disease", Dept. Health & Human Services Public Health Service Grant Application, funded in 1988.

Noszek & Siman, "An Excitatory Amino Acid Activates Calpain I and Structural Protein Breakdown *In Vivo*", *Soc. Neurosci. Abstr.* 1684:466.11 (1987).

Otsuka & Goll, "Purification of the $Ca^{2+}$-dependent Proteinase Inhibitor from Bovine Cardiac Muscle and Its Interaction with the Millimolar $Ca^{2+}$-dependent Proteinase", *J. Biol. Chem.* 262:5839–5851 (Apr. 25, 1987).

Ponte et al., "A New A4 amyloid mRNA contains a domain homologous to serine proteinase inhibitors", *Nature* 331:525–527 (Feb. 11, 1988).

Siman et al., "Excitatory Amino–Acid Induced Neurotoxicity: Blockade by Protease Inhibitors", *Soc. Neurosci. Abstr.* 1684:466.12 (1987).

Spencer et al., "Guam Amyotrophic Lateral Sclerosis–Parkinsonism–Dementia Linked to A Plant Excitant Neurotoxin", *Science* 237:517–522 (Jul. 31, 1987).

Takahashi–Nakamura et al., "Purification and Characterization of an Inhibitor of Calcium–Activated Neutral Protease from Rabbit Skeletal Muscle", *J. Biochem.* 90:1583–1589 (1981).

Takano & Murachi, "Purification and Some Properties of Human Erythrocyte Calpastatin", *J. Biochem.* 92:2021–2028 (1982).

Takano et al., "Molecular Diversity of Calpastatin in Mammalian Organs", *Biochem. & Biophys. Res. Comm.* 122:912–917 (Aug. 16, 1984).

(List continued on next page.)

*Primary Examiner*—Christine M. Nucker
*Assistant Examiner*—Jeffrey Stucker
*Attorney, Agent, or Firm*—Sterne, Kessler, Goldstein & Fox, P.L.L.C.

[57] ABSTRACT

This invention is directed to two highly purified neural calcium-activated neutral proteinase (CANP or calpain) inhibitors, known as high molecular weight calpastatin (HMWC) and low molecular weight calpastatin (LMWC). The invention also relates to recombinant DNA molecules which code for, and antibodies which bind to these proteins. The present invention is further directed to the use of these calpastatin proteins.

2 Claims, 14 Drawing Sheets

OTHER PUBLICATIONS

Takano et al., "Two different molecular species of pig calpastatin", *Biochem. J.* 235:97–102 (1986).

Takano et al., "Multiple Forms of Calpastatin in Pig Brain", *Biochem. Int.* 19:633–643 (Sep. 1989).

Vitto & Nixon, "Calcium–Activated Neutral Proteinase of Human Brain: Subunit Structure and Enzymatic Properties of Multiple Molecular Forms", *J. Neurochem.* 47:1039–1051 (1986).

Wolozin & Davies, "Characterization of the ALZ–50 Antigen", *Neurosc. Abstracts* 944:259.7 (1986).

Yamato et al., "The Appearance of a 34,000–Dalton Inhibitor of Calpain ($Ca^{2+}$–Dependent Cysteine Proteinase) in Rat Liver After the Administration of Phenylhydrazine", *Biochem. & Biophys. Res. Comm.* 115:715–721 (Sep. 15, 1983).

Hamakubo et al., Distributional and Developmental Variations of Multiple Forms of Calpastatin in Mouse Brain, *J. Enzyme Inhibition* 3:203–210 (1990).

Murachi, T. et al., "Multiple Forms of Calpastatin in the Brain," *J. Cell Biol.* 107:392a: Abstract No. 2233 (Dec. 1988).

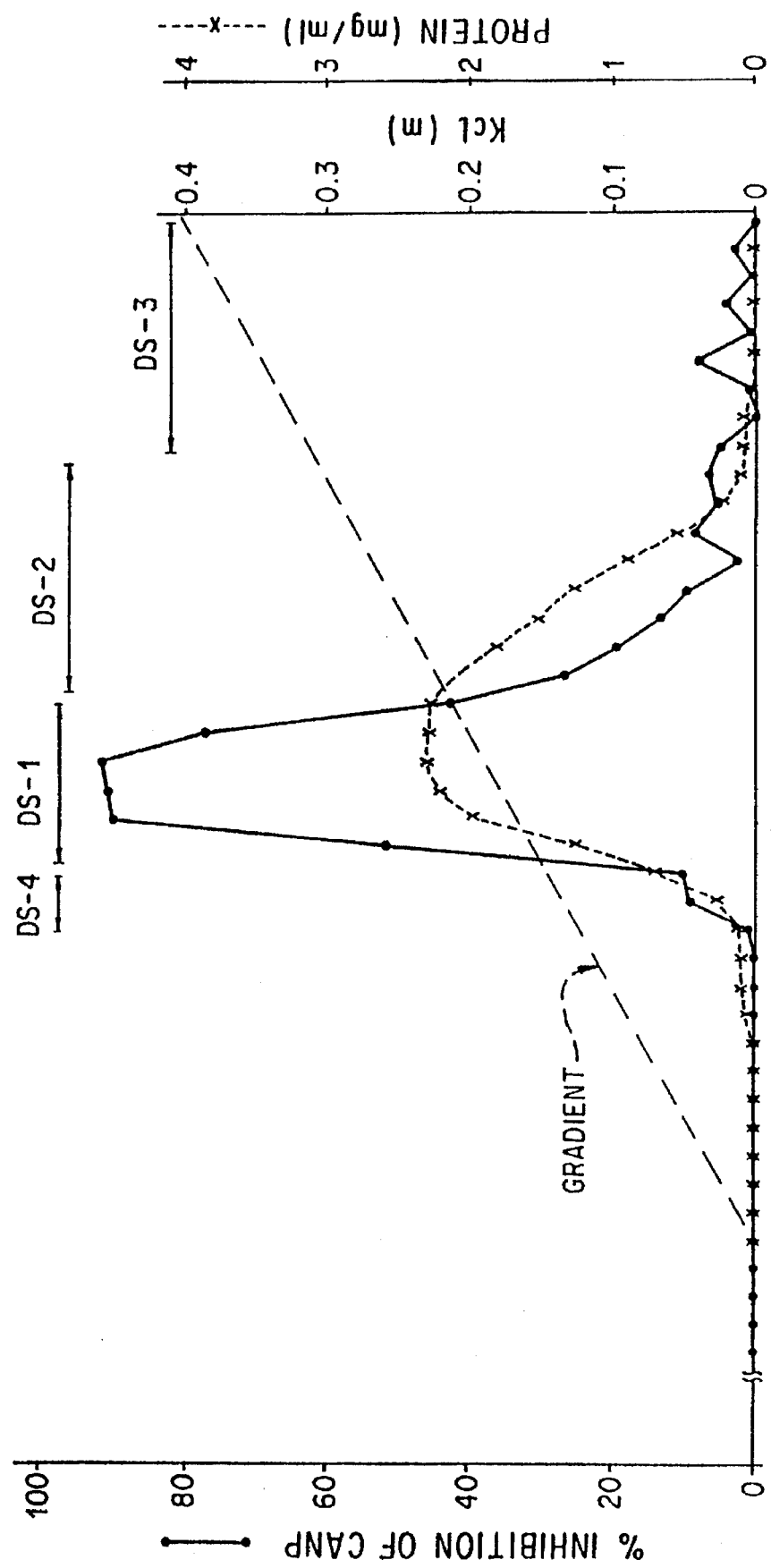
F I G. 5

NEURAL CALCIUM-ACTIVATED NEUTRAL PROTEINASE INHIBITORS

CROSS-REFERENCE TO RELATED APPLICATION

This application is a divisional, of application Ser. No. 07/735,611, filed Jul. 25, 1991 now U.S. Pat. No. 5,340,922 is a continuation-in-part of application Ser. No. 07/356,458, filed in the U.S. Patent and Trademark Office on May 25, 1989, now abandoned, which is a continuation-in-part of application Ser. No. 07/200,141, filed in the U.S. Patent and Trademark Office on May 31, 1988, now abandoned. The contents of the parent application (Ser. No. 07/200,141) and continuation-in-part application (Ser. No. 07/356,458) are incorporated by reference herein.

FIELD OF THE INVENTION

This invention is directed to two highly purified neural calcium-activated neutral proteinase (CANP or calpain) inhibitors, known as high molecular weight calpastatin (HMWC) low molecular weight calpastatin (LMWC). The invention also relates to recombinant DNA molecules which code for, and antibodies which recognize and bind to, these proteins. The present invention is further directed to the uses for these calpastatin proteins.

BACKGROUND OF THE INVENTION

Proteolysis has been implicated not only in protein turnover, but also in the regulation of other physiological functions, such as, protein translocation, fibrinolysis, digestion, hormone maturation, and fertilization (see, e.g., *Protein Degradation in Health and Disease* in: CIBA Foundation Symposium 75, published by Excerpta Medica, NY (1980)). Responsible for such functions are proteinases, which enzymatically catalyze the degradation of protein substrates.

A number of diverse mechanisms exist which play important roles in the regulation of proteolytic activity. Particularly important mechanisms include modulation of proteinase activity, modulation of substrates, localization of proteinases, and sequestration of proteinases into vesicles (see, e.g., *Protein Degradation in Health and Disease* in: CIBA Foundation Symposium 75, published by Excerpta Medica, NY (1980)).

Calcium-activated neutral proteinase (CANP, or calpain), a non-lysosomal cysteine proteinase, is believed to participate in various intracellular processes mediated by calcium (Waxman, L., *Methods Enzymol.* 80:644–680 (1981); Imahori, K., In: *Calcium and Cell Function*, Vol. 3, pp. 473–487 (W. Y. Cheung, ed.), Academic Press, N.Y. (1982); Murachi, *Trends Biochem. Sci.* 8:167–169 (1983); Mellgren, R., *FASEB J.* 1:110–115 (1987); Schollmeyer, J. E., *Science* 240:911–913 (1988); Watanake et al. *Nature* 342:505–511 (1989)). CANPs comprise a family of enzymes that are widely distributed in mammalian and avian cells (Murachi et al., *Trends in Biochem. Sciences* 8:167–169 (1983)).

The potential activity of CANPs in cells appears to greatly exceed the physiological needs. For example, when maximally expressed under experimental conditions, CANPs in retinal ganglion cells can hydrolyze more than 50% of the entire content of axonal proteins within 5–15 minutes (Nixon et al., *J. Neurosci.* 6:1252–1263 (1986)). Given this enormous potential activity, it is not surprising that various mechanisms exist to regulate calcium-dependent proteolysis in vivo, including cellular calcium levels, modulation of the enzyme's sensitivity to calcium, autolytic activation, and its interaction with endogenous activating and inhibitory factors.

The role of CANPs in mediating cellular responses to the calcium signal is becoming widely accepted (Suzuki et al., *FEBS Lett.* 220:271–277 (1987)). The evidence linking calcium-activated proteolysis to key regulatory processes is of particular interest. The work of Pontremoli et al., *PNAS USA* 84:3604–3608 (1987), for example, has provided direct evidence in intact cells for a role of CANP in the modulation of responses to external stimuli mediated by protein kinase C.

CANPs have been implicated in neurobiological phenomena ranging from transmembrane signaling and synaptic plasticity to disease-related neuronal degeneration and cell death. This suspected functional diversity reflects the existence of multiple CANPs and a complex regulation which includes changes in calcium concentration, interaction with specific endogenous inhibitors (calpastatins), autolytic conversion of pro-forms to more active enzymatic forms, ability of the protease to translocate to different cellular sites, and influences of protein substrate properties.

The ability of CANPs to modulate protein kinase C and other protein kinases suggests that these proteinases are an important component of the regulatory system mediating the transduction of extracellular calcium signals. The ability of CANP to carry out limited proteolytic cleavage and thereby activate certain enzymes, including protein kinase C, emphasizes the potential creative functions of proteolysis and implies that the actions of CANP may be amplified intracellularly in provocative ways.

Because CANPs are particularly well-represented in neurons (Nixon et al., *J. Neurochem.* 6:1252–1263 (1986); Nixon, R. A., *J. Neurochem.* 6:1264–1271 (1986); Hamakabu et al., J. Neurosci. 6:3103–3111 (1986)), various neurobiological roles have been proposed for them, including synaptic modulation (Lynch et al., *Science* 224:1057–1063 (1984)), the post-translational modification and degradation of cytoskeletal proteins (reviews: Nixon, R. A., In: *Neurofilaments* (Marotta, C. A., eds.), pp. 117–154, Univ. Minnesota Press, Minneapolis, Minn. (1983); Schlaepfer, in: *Neurofilaments*, pp. 57–85, C. A. Marotta (ed.), Univ. of Minnesota Press (1983)) and the modification of membrane receptors (Baudry et al., *Science* 212:937–938 (1981)). CANPs appear to be involved in the postsynaptic events of long-term potentiation (Staubli et al., *Brain Res.* 444:153–158 (1988)), and the mounting evidence for a regulatory role of CANPs in protein kinase C modulation (Suzuki et al., *FEBS Lett.* 220:271–277 (1987)) is consistent with a role in presynaptic mechanisms of long-term potentiation (Akers et al., *Science* 231:587–589 (1986)).

Although the involvement of proteolytic systems in cell death is clearly established, there has been a traditional bias toward regarding proteolysis as an end-stage phenomenon or as merely a scavenging mechanism for cellular debris. This traditional role for proteolytic enzymes has been revised by a new appreciation of the varied regulatory roles of proteolytic enzymes in nearly every aspect of cellular function, including neurophysiological function.

Increased interest in the role of excitatoxins in mechanisms of cell death in neurodegenerative disease and related disorders (Spencer et al., *Science* 237:517–519 (1987)) also implicates CANPs. Rapid influx of calcium can lead directly to an activation of latent CANP. Some recent studies demonstrate that excitatoxins activate CANP and induce structural protein breakdown in vivo (Noszek, et al., *Soc. Neu-* rosci. Abstr. 13:1684 (1987)) and that CANP inhibitors reduced the damage produced by kainate, NMDA and quisqualate (Siman et al., *Soc. Neurosci. Abstr.* 13:1684 (1987)).

Such considerations are especially pertinent to an examination of Alzheimer's Disease pathogenesis, for example. It has been found that the inactivation of CANP with a specific monoclonal antibody inhibits the conversion of membrane-bound protein kinase C to a soluble calcium-independent form, thereby increasing the production of superoxides and stimulating the phosphorylation of membrane proteins. These effects are directly relevant to known mechanisms of cell death such as free radical-induced cellular damage, secondarily increased $Ca^{2+}$ influx (Cross et al., *Ann. Int. Med.* 107:526–545 (1987)), and the structural abnormalities found in Alzheimer's Disease brain such as altered phosphorylation of cytoskeleton proteins (tau) and membrane damage leading to altered amyloid precursor protein processing (Dyrks et al., *EMBO J.* 7:949–957 (1988)).

The conspicuous susceptibility of cytoskeletal proteins to CANPs and the relative enrichment of CANPs in neurons has focused particular attention on these proteases as regulators of neuronal cytoskeleton dynamics.

By what mechanisms CANP activity may become down-regulated and thereby give rise to intracellular accumulations of cytoskeletal proteins or protein fragments in affected Alzheimer's Disease neurons, and at what stage calcium influx ultimately increases to activate latent CANPs to cause irreversible cell death, remain unanswered questions of considerable importance to Alzheimer's Disease and other late-onset neurodegenerative disorders. That is why the regulators of CANP activity, such as endogenous inhibitors, are so important.

Calpastatins, the specific protein inhibitors of CANP, are also widely distributed among tissues. First identified in 1978 (Waxman et al., *J. Biol. Chem.* 253:5888–5891 (1978)), calpastatins have since been purified from several different sources. Although each of the purified species shares the properties of heat stability and strict specificity for CANP, there is no consensus on the number of forms of calpastatin within single cells or among different cell types. The recent characterization of a calpastatin cDNA isolated from a rabbit cDNA library (Emori et al., *Proc. Natl. Acad. Sci. USA* 84:3590–3594 (1987)) revealed a deduced sequence of 718 amino acid residues ($M_r$=76,964) containing four consecutive internal repeats of approximately 140 amino acid residues, each expressing inhibitory activity (Emori, et al., ibid. (1987)). This deduced molecular weight is significantly lower than the molecular weight of rabbit skeletal muscle calpastatin ($M_r$=110,000), suggesting that the inhibitor migrates anomalously on SDS gels and may be post-translationally modified.

Other studies suggest that additional molecular forms of calpastatin may be present in tissues. Although 110 kDa calpastatin is observed in rabbit and bovine skeletal muscle (Nakamura et al., *J. Biochim.* 98:757–765 (1985); Otsuka et al., *J. Biol. Chem.* 262:5839–5851 (1987)), porcine cardiac muscle (Takano et al., *J. Biochem.* 235:97–102 (1986)) and human liver (Imajoh et al., *FEBS Lett.* 187:47–50 (1984)), other molecular forms of calpastatin have also been isolated, including a 68 kDa form from chick skeletal muscle (Ishiura et al., *Biochem. Biophys. Acta* 701:216–223 (1982)) and porcine erythrocytes (Takano et al., *J. Biochem.* 235:97–102 (1986)), a 50 kDa heterodimer from rabbit skeletal muscle (Nakamura et al., *J. Biochem.* 96:1399–1407 (1984)) and 34 kDa forms from rabbit skeletal muscle (Takahashi-Nakamura et al., *J. Biochem.* 90:1583–1589 (1981)) and rat liver (Yamato et al., *Biochem. Biophys. Res. Comm.* 115:715–721 (1983)). The sensitivity of calpastatin to proteolysis has suggested that smaller polypeptide chains containing inhibitory activity might be derived from larger precursors during purification, or in vivo. Although certain of these low molecular weight calpastatins resemble the higher molecular weight forms, their derivation from the same gene product has not been established.

Although the activity of calpastatins in the nervous system is considerable, little else is known about the properties of these proteins and how they regulate calcium-mediated proteolysis in neural cells.

SUMMARY OF THE INVENTION

The inventor initiated studies on neural calpastatins, the calpain inhibitory factors. As part of this research, two related endogenous neural, especially human brain, calcium-activated neutral proteinase (CANP or calpain) inhibitors, known as high molecular weight calpastatin (HMWC) and low molecular weight calpastatin (LMWC) were identified and purified.

The high molecular weight (HMW) calpastatin (HMWC) is a protein with a native molecular weight of 300 kilodaltons (kDa) which was purified to homogeneity from postmortem human brain. The denatured molecular weight of HMWC was determined to be 41 kilodaltons. The 41 kDa polypeptide as well as the native 300 kDa protein were heat stable and specific for calcium-activating neutral proteinases. Antibodies raised against the purified protein reacted selectively with the 41 kDa polypeptide, in addition to forming an immunocomplex with the native protein. The purified inhibitor exhibited an isoelectric point of 4.5 (pI= 4.5) by polyacrylamide gel isoelectric focusing.

The low molecular weight (LMW) calpastatin (LMWC) identified has a native molecular weight of 60 kDa. The low molecular weight calpastatin (LMWC) has a denatured molecular weight of 31 kDa and a pI range of 4.2–4.7. LMWC is heat stable and specific for calcium-sensitive forms of CANP.

The LMWC and HMWC show a lack of immunologic relatedness. None of the antibodies raised against the HMWC cross reacted with the 60 kDa or 31 kDa LMWC proteins in unfractionated brain tissue or in purified form by Western blot analysis. Furthermore, analysis of the N-terminal sequence of each of the peptides, i.e., 41 and 31 kDa, revealed little if any homology between these proteins. Although some observations suggest that the low molecular weight calpastatin may be proteolytic products of the high molecular weight form, no homology was found by protein sequencing, indicating that the calpastatin proteins of the present invention are different.

The amino acid composition of HMWC and LMWC is distinct from that of previously reported pig heart and rabbit liver calpastatins (Emori et al., *PNAS USA* 84:3590–3594 (1987) and Murachi et al., *Biochem. J.* 84:3590(1987)).

The inhibitors of the present invention have major implications for understanding, diagnosing, and controlling various neurodegenerative disorders.

DESCRIPTION OF THE FIGURES

FIG. 5. DEAE-Sepharose 4B chromatography of Ultrogel AcA-44 purified HMW calpastatin: CANP inhibitory activity (solid lines) and relative protein concentration (broken lines). The active fractions corresponding to HMWC indicated in FIG. 4 were pooled, adjusted to 0.3M KCl and applied to a DEAE-Sepharose 4B column. HMWC activity was eluted with buffer D as described in the Examples section.

DETAILED DESCRIPTION OF THE INVENTION

Figure 1:
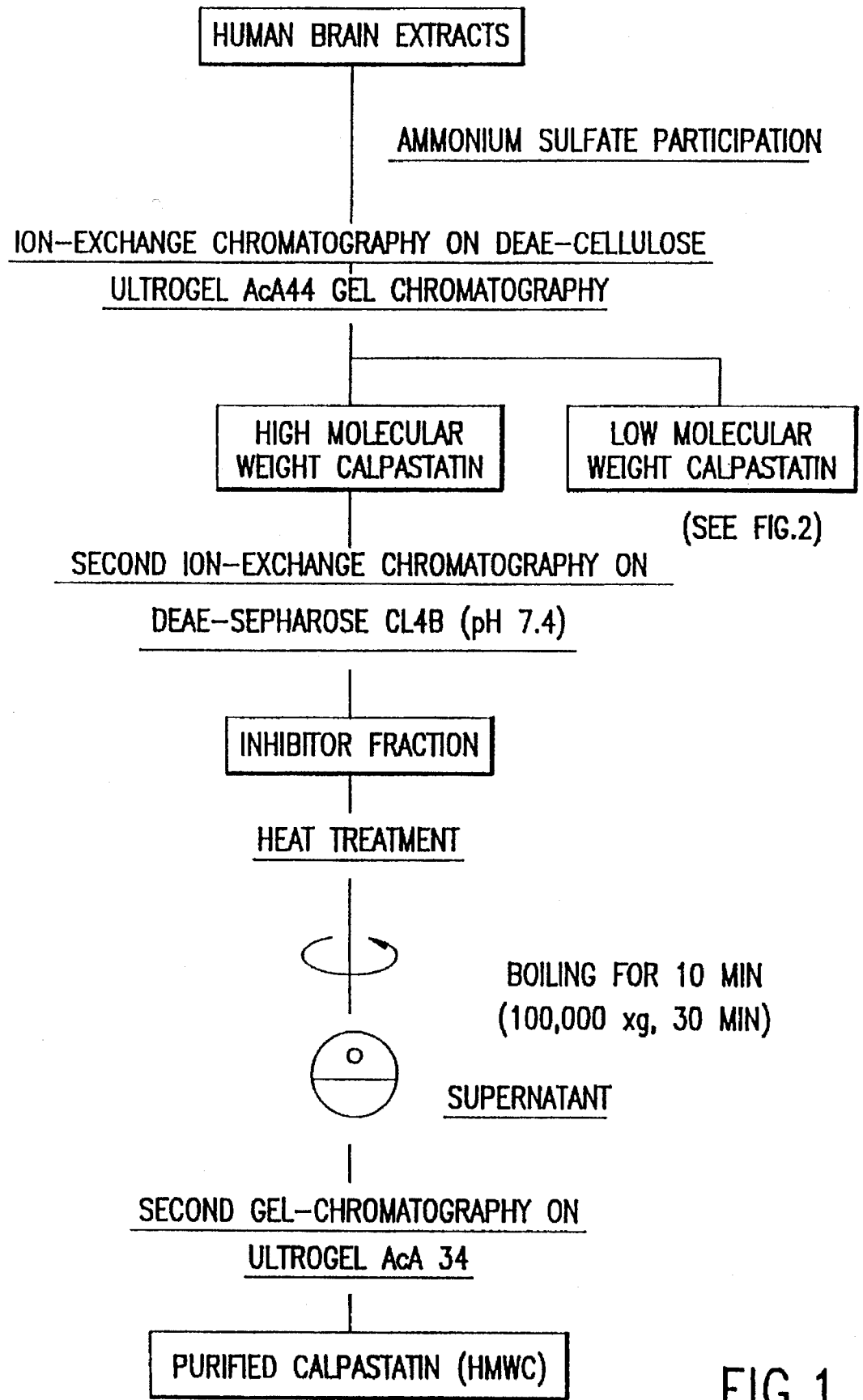
FIG. 1. Flow diagram for the purification of high molecular weight calpastatin from human brain. Native molecular weight: MW—300,000; reduced and denatured HMWC on SDS-PAGE: MW—41,000; isoelectric point: 4.5; Immunocharacterization: (Sheep IgG: I-2-7); 2-D gel immunoblotting—a single spot (MW 41,000,pI: 4.5); native calpastatin formed complex with I-2-7.

A. Low and High Molecular Weight Calpastatin

Calcium-activated neutral proteinases (CANPs or calpains) are a family of cysteine endopeptidases in vertebrate tissues. The physiological roles proposed for calpains include activation of enzymes (especially protein kinases), modification of receptor binding properties, participation in general protein turnover, modification and degradation of cytoskeletal proteins, and regulation of membrane-cytoskeleton interactions. In addition, calcium-activated proteolysis partly mediates the degeneration following axotomy and axonal injury and has been proposed as a pathogenetic factor in certain neurodegenerative disorders.

Endogenous protein inhibitors of calpains, called calpastatins, are heat-stable polypeptides with high specificity for calcium-dependent proteinases. Calpastatins are essential factors in the in vivo regulation of CANP activity, and perturbations of this ratio of inhibitor to enzyme in non-neural tissues have the predicted consequences on CANP activity in cells.

According to this invention, two forms of neural calpastatin proteins have been identified and purified: a high molecular weight calpastatin (HMWC) and a low molecular weight calpastatin (LMWC).

The HMW calpastatin is a protein with a molecular weight of 300 kDa, with a denatured molecular weight of 41 kDa. The HMWC is heat stable and specific for calcium-activating neutral proteinases. Antibodies raised against HMWC react selectively with the 41 kDa peptide on immunoblots after 2-D gel protein analysis. This antibody also selectively binds to the native 300 kDa protein, forming an immunocomplex.

The purified HMWC exhibited an isoelectric point of 4.5 by polyacrylamide gel isoelectric focusing. The amino acid composition of HMWC is shown in Table 3, and the N-terminal amino acid sequence (19 amino acids) of HMWC 41 kDa peptide was determined as follows:

$NH_2$-X-Met-Pro-Pro-Glu-Pro-Ala-Thr-Leu-Lys-Gly-X-Val-Pro-Asp-Asp-Ala-Val-Glu (SEQ ID NO: 1)

wherein X represents an unknown amino acid residue.

The amino acid sequence of HMWC is different from any other calpastatin reported in the past, distinguishing this protein as a distinct and novel form of calpastatin.

The present invention also concerns a LMWC protein. The LMWC is a heat-stable protein which is specific for calcium-sensitive forms of CANP. The molecular weight of this protein was determined to be 60 kDa. The native protein consisted of a 31 kDa dimer with a pI range of 4.2–4.7 on isoelectric focusing gels.

The amino acid composition of LMWC is disclosed in Table 6. The N-terminal sequence of LMWC for the first 20 amino acid residues was determined as follows:

$NH_2$-X-Glu-Lys-Glu-Thr-Lys-Glu-Glu-Gly-Lys-Pro-Lys-Gln-Gln-Gln-X-X-Lys-Glu-Lys (SEQ ID NO: 2)

wherein X represents an unknown amino acid residue.

HMWC and and LMWC show a lack of immunologic relatedness. None of the antibodies raised against the HMWC cross reacted with LMWC in unfractionated brain tissue or in purified form by Western blot analysis. Furthermore, analysis of the N-terminal sequence of each of the peptides, i.e., 41 and 31 kDa, revealed little if any homology between these proteins.

The purified HMWC differs in molecular weight, amino acid composition, and isoelectric point from the calpastatin isolated previously from chicken (Ishiura et al., *Biochim. Biophys. Acta* 701:216–223 (1982) and rabbit (Takahashi-Nakamura et al., *J. Biochem.* 96:1399–1407 (1981) skeletal muscle and differs in molecular weight from the inhibitor isolated from human erythrocytes (Murakami et al., *J. Biochem* 90:1798–1816 (1981)). In addition, the calpastatin proteins of the present invention differ in size from a number of calpastatin proteins isolated from other sources including bovine cardiac muscles which were reported to contain a monomeric inhibitor of 145,000 daltons (Mellgren et al., *ABB* 22:779–786 (1983)). DeMartino and Croall purified a dimeric inhibitor of 125,000 daltons from rat liver (*ABB*, 232:713–720 (1984).

The amino acid composition of the 41 kDa peptide of HMWC and the 31 kDa peptide of LMWC are distinct from that of previously reported pig heart and rabbit liver calpastatins (Emori et al., *PNAS USA* 84:3590–3594 (1987) and Takano et al., *Biochem. J.* 235:97–102 (1986)).

B. Isolation of Low and High Molecular Weight Calpastatin

In accordance with this invention, LMWC and HMWC can be isolated from a sample containing the enzymes. Any sample that contains the enzymes may be used as a starting material according to the methods described in this invention. The sample will typically be neural tissue, particularly brain tissue and more particularly cerebral cortex tissue, and can be either gray or white matter. The neural tissue can be from any vertebrate source, preferably from mammalian brain and more preferably from human brain. However, the calpastatins described by the present invention have also been identified in mouse and bovine brain, spinal cord, and murine optic nerve. The calpastatin proteins of the present invention may also be isolated from host cells which express the recombinant calpastatin protein(s).

The isolation and purification of calpastatin proteins of the present invention are described herein from a human cerebral cortex sample, although it is to be understood that other brain samples could be used as the source material.

According to this invention, LMWC and HMWC are purified to homogeneity by a series of chromatographic steps. The proteins were isolated using methods that did not require exposing the inhibitors to calcium treatment, a factor that might alter the properties of calpastatin. Although the purification procedure involved a heat treatment step, this treatment was found not to alter the properties of these proteins.

The tissue sample according to the present invention was first homogenized in a buffer solution; HMWC and LMWC separated into the supernatant fraction following centrifugation. The calpastatin proteins of the present invention were then purified to homogeneity by a number of biochemical purification techniques including precipitation, ion exchange, gel filtration, hydrophobic interaction, two dimensional gel electrophoresis and isoelectric focusing gels.

The specific techniques for isolation and purification of the HMWC calpastatin of the present invention involved anion exchange on diethylaminoethyl (DEAE)-cellulose, gel filtration on Ultrogel AcA-44, a DEAE-Sepharose CL4B ion-exchange column, heat-treatment (100° C., 5 min) and Ultrogel AcA34 gel chromatography. Purification techniques for LMW calpastatin, on the other hand, involved anion exchange on DEAE-cellulose, gel filtration on Ultrogel AcA44, ion exchange on CM-cellulose, affinity chromatograpahy on Con A-Sepharose, heat treatment, and Sephacryl-300 chromatography. One of skill in the art will know of equivalents to these particular chromatographic columns which may be employed in isolating and purifying the proteins of this invention. Furthermore, as will be apparent to those of skill in the art, affinity chromatography, for example, with antibodies specific for HMWC or LMWC, may be used to purify the proteins of the present invention. Techniques of immunoaffinity purification are described by Harlow et al., In: *Antibodies, A Laboratory Manual*, Coldspring Harbor, N.Y. (1988) which is herein incorporated by reference.

Figure 2:
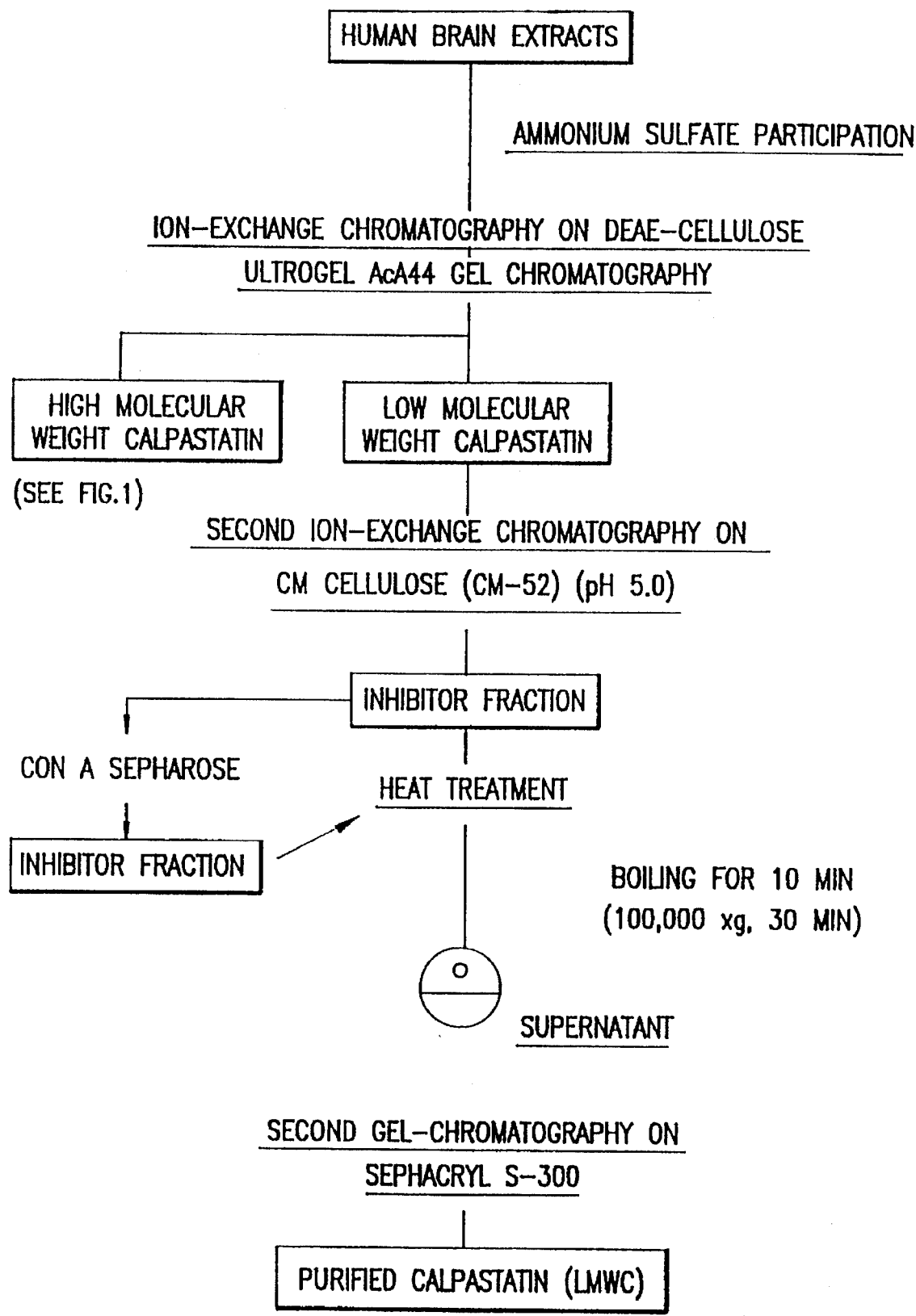
FIG. 2. Flow diagram for the purification of low molecular weight calpastatin from human brain. Native molecular weight: MW—60,000; reduced and denatured LMWC on SDS-PAGE: MW 31,000; isoelectric point: pI: 4.2–4.7; two-dimensional gel electrophoresis: LMWC 31 KDa (pI 4.2–4.7).

Although differing slightly in their affinity for DEAE-cellulose, both calpastatins were not separated at this step. Gel filtration chromatography on Ultrogel AcA 44, however, resolved two peaks of inhibitory activity, designated high molecular weight calpastatin (HMWC) and low molecular weight calpastatin (LMWC). The purification schemes for HMWC and LMWC are represented in FIGS. 1 and 2, respectively.

Calpastatin activity was measured as the inhibition of $^{14}C$-azocasein degradation by purified human brain calpain II. The HMWC and the LMWC, separated at the Ultrogel step, should each have accounted for about half of the total inhibitory activity in the brain tissue. The two calpastatins exhibited approximately the same specific activities.

In the process of this invention, HMWC was purified 964-fold while LMWC was purified 528-fold, as measured by inhibitor activity, with approximately 19.5% recovery in HMWC and 15% recovery in LMWC of total activity.

In a preferred embodiment, without being limiting, a purification scheme for low molecular weight calpastatin with a molecular weight of about 60 kDa and having an activity defined as the ability to inhibit the activity of purified calcium-activated neutral proteinase, would comprise:

A. recovering crude LMWC from a neural sample;

B. subjecting said crude LMWC from step (A) to ion exchange chromatography to obtain active fractions of LMWC as defined as the ability to inhibit the activity of purified calcium-activated neutral proteinase;

C. subjecting said active fractions of LMWC from step (B) to gel filtration to obtain partially purified LMWC;

D. subjecting said partially purified LMWC from step (C) to ion exchange chromatography to obtain partially purified LMWC;

E. heat treating said partially purified LMWC from step (D); and

F. purifying said partially purified LMWC from step (E) by gel filtration to obtain substantially pure LMWC.

Similarly, in a preferred embodiment, without being limited, a purification scheme for high molecular weight calpastatin (HMWC) with a molecular weight of about 300 kDa, said HMWC having one subunit polypeptide with a molecular weight of about 41 kDa, having an enzyme activity as defined as the ability to inhibit the activity of purified calcium-activated neutral proteinase, would comprise:

(a) recovering crude HMWC from a neural sample;

(b) subjecting said crude HMWC from step (a) to ion exchange chromatography to obtain active fractions of HMWC by defined as the ability to inhibit the activity of purified calcium-activated neutral proteinase;

(c) subjecting said active fractions of HMWC from step (b) to gel filtration to obtain partially purified HMWC;

(d) subjecting said partially purified HMWC from step (c) to ion exchange chromatography to obtain partially purified HMWC;

(e) heat treating said partially purified HMWC from step (d);

(f) subjecting said partially purified HMWC from step (e) to gel filtration; and (g) obtaining substantially purified HMWC.

Using the above-described series of purification steps, calpastatin was substantially purified over the cell extract. As used herein, the term "substantially pure" or "substantially purified" is meant to describe HMWC or LMWC which is substantially free of any compound normally associated with the enzyme in its natural state, i.e., substantially free of contaminating protein and carbohydrate components. The term is further meant to describe calpastatins of the present invention which are homogeneous by one or more purity or homogeneity characteristics used by those of skill in the art. For example, substantially pure calpastatin proteins will show constant and reproducible characteristics within standard experimental deviations for parameters such as the following: molecular weight, chromatographic techniques, and such other parameters. The term is not meant to exclude the presence of minor impurities which do not interfere with the biological activity of the enzyme, and which may be present, for example, due to incomplete purification.

C. Cloning Calpastatin Genes

Any of a variety of procedures may be used to clone the calpastatin genes of the present invention. One such method entails analyzing a shuttle vector library of DNA inserts (derived from brain tissue which expresses calpastatin proteins) for the presence of an insert which contains the calpastatin genes. Such an analysis may be conducted by transfecting cells with the vector and then assaying for expression of the calpastatin inhibitory activity. The preferred method for cloning these genes entails determining the amino acid sequence of the calpastatin proteins. To accomplish this task the desired calpastatin protein may be purified and analyzed by automated sequencers. Alternatively, each protein may be fragmented as with cyanogen bromide, or with proteases such as papain, chymotrypsin or trypsin (Oike, Y. et al., *J. Biol. Chem.* 257:9751–9758 (1982); Liu, C. et al., *Int. J. Pept. Protein Res.* 21:209–215 (1983)). Although it is possible to determine the entire amino acid sequence of these proteins, it is preferable to determine the sequence of peptide fragments of these molecules. If the peptides are greater than 10 amino acids long, the sequence information is generally sufficient to permit one to clone a gene such as the gene for a particular nuclease or ligand.

The N-terminal amino acid sequence for the calpastatin proteins of the present invention was determined and is depicted in tables 5 and 7.

Once one or more suitable peptide fragments have been sequenced, the DNA sequences capable of encoding them are examined. Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon. Although occasionally such amino acid sequences may be encoded by only a single oligonucleotide, frequently the amino acid sequence can be encoded by any of a set of similar oligonucleotides. Importantly, whereas all of the members of the set contain oligonucleotides which are capable of encoding the peptide fragment and, thus, potentially contain the same nucleotide sequence as the gene which encodes the peptide fragment, only one member of the set contains a nucleotide sequence that is identical to the nucleotide sequence of this gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

In a manner exactly analogous to that described above, one may employ an oligonucleotide (or set of oligonucleotides) which have a nucleotide sequence that is complementary to the oligonucleotide sequence or set of sequences that is capable of encoding the peptide fragment.

A suitable oligonucleotide, or set of oligonucleotides Which is capable of encoding a fragment of the desired calpastatin gene (or which is complementary to such an oligonucleotide, or set of oligonucleotides) is identified (using the above-described procedure), synthesized, and hybridized, by means well known in the art, against a DNA or a cDNA preparation depending upon the source of the gene. Typically, isolation of eukaryotic genes is done by screening a cDNA library, while a DNA library is used to isolate prokaryotic genes. Techniques of nucleic acid hybridization are disclosed by Maniatis, T. et al., In: *Molecular Cloning, a Laboratory Manual*, Second Edition, Coldspring Harbor, N.Y. (1989), and by Haymes, B. D. et al., In: *Nucleic Acid Hybrization, a Practical Approach*, IRL Press, Washington, D.C. (1985), which references are herein incorporated by reference. The source of the cDNA used according to the present invention will preferably be obtained by extracting RNA from human brain cells.

Techniques such as, or similar to, those described above have successfully enabled the cloning of genes for streptavadin (Argarana et al., *Nucleic Acids Research* 14(4):1871–1882 (1986), avidin (Kulomma et al., *J. Cell Biochem. Supp.* part 2:210 (1988), human hepatitis type B antibody (Hong et al., *Korean J. Biochem.*, 18(1):7–18 (1986)), human aldehyde dehydrogenases (Hsu, L. C. et al., *Proc. Natl. Acad. Sci. USA* 82:3771–3775 (1985)), fibronectin (Suzuki, S. et al., *Eur. Mol. Biol. Organ. J.* 4:2519–2524 (1985)), the human estrogen receptor gene (Walter, P. et al., *Proc. Natl. Acad. Sci. USA* 82:7889–7893 (1985)), tissue-type plasminogen activator (Pennica, D. et al., *Nature* 301:214–221 (1983)) and human term placental alkaline phosphatase complementary DNA (Kam, W. et al., *Proc. Natl. Acad. Sci. USA* 82:8715–8719 (1985)).

In a alternative way of cloning calpastatin genes, a library of expression vectors is prepared by cloning DNA or cDNA, from a cell capable of expressing calpastatin into an expression vector. The library is then screened for members capable of expressing a protein which binds to anti-HMWC or anti-LMWC antibody, and which has a nucleotide sequence that is capable of encoding polypeptides that have the same amino acid sequence as the calpastatin proteins of the present invention, or fragments or variants thereof.

D. Expression of Calpastatin Genes

DNA molecules composed of a calpastatin gene or at least portions of these genes can be operably linked into an expression vector and introduced into a host cell to enable the expression of these proteins by that cell. Two DNA sequences (such as a promoter region sequence and a desired calpastatin protein encoding sequence) are said to be operably linked if the nature of the linkage between the two DNA sequences does not (1) result in the introduction of a frame-shift mutation, (2) interfere with the ability of the promoter region sequence to direct the transcription of the desired protein encoding gene sequence, or (3) interfere with the ability of the desired protein gene sequence to be transcribed by the promoter region sequence.

A DNA sequence encoding a calpastatin protein may be recombined with vector DNA in accordance with conventional techniques. The present invention encompasses the expression of the desired fusion proteins in either prokaryotic or eukaryotic cells. Eukaryotic hosts include yeast (especially Saccharomyces), fungi (especially Aspergillus), mammalian cells (such as, for example, human or primate cells) either in vivo, or in tissue culture.

Yeast and mammalian cells provide substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeasts recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells of fibroblast origin such as VERO or CHO-K1, and their derivatives. For a mammalian host, several possible vector systems are available for the expression of the desired fusion protein. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

The expression of the desired fusion protein in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired fusion protein does not contain any intervening codons which are capable of encoding a methionine (i.e., AUG). The presence of such codons results either in the formation of a fusion protein (if the AUG codon is in the same reading frame as the desired fusion protein encoding DNA sequence) or a frame-shift mutation (if the AUG codon is not in the same reading frame as the desired fusion protein encoding sequence).

The expression of the calpastatin proteins can also be accomplished in procaryotic cells. Preferred prokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E. coli* K12, and other enterobacteria (such as *Salmonella typhimurium* or *Serratia marcescens*), and various Pseudomonas species. The prokaryotic host must be compatible with the replicon and control sequences in the expression plasmid.

To express the desired calpastatin proteins in a prokaryotic cell (such as, for example, *E. coli*, *B. subtilis*, Pseudomonas, Streptomyces, etc.), it is necessary to operably link the desired fusion protein encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the b-lactamase gene of pBR322, etc. Examples of inducible prokaryotic promoters include the major right and left promoters of bacteriophage λ ($P_L$ and $P_R$), the trp, recA, lacZ, lacI, gal, and tac promoters of *E. coli*, the a-amylase (Ulmanen, I., et al., *J. Bacteriol.* 162:176–182 (1985)), the s-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., NY (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream from the gene-encoding sequence. Such ribosome binding sites are disclosed, for example, by Gold, L., et al. (*Ann. Rev. Microbiol.* 35:365–404 (1981)).

The desired protein encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired receptor molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or vital vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982)).

For a mammalian host, several possible vector systems are available for expression. One class of vectors utilizes DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

Preferred prokaryotic vectors include plasmids such as those capable of replication in *E. coli* such as, for example, pBR322, ColE1, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, NY (1982), pp. 307–329). Suitable Streptomyces plasmids include pIJ101 (Kendall, K. J., et al., *J. Bacteriol.* 169:4177–4183 (1987)), and Streptomyces bacteriophages such as ϕC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

Once the vector or DNA sequence containing the constructs has been prepared for expression, the DNA constructs may be introduced into an appropriate host. Various techniques may be employed, such as protoplast fusion, calcium phosphate precipitation, electroporation or other conventional techniques. After the fusion, the cells are grown in media and screened for appropriate activities. Expression of the sequence results in the production of the recombinant calpastatin proteins of the present invention.

E. Purification of Recombinant Calpastatin Proteins

The calpastatin proteins of this invention can be produced by fermentation of the recombinant host containing the cloned calpastatin genes. The recombinant host, such as mammalian cells producing the cloned proteins, can be grown and harvested according to techniques well known in the art.

The recombinant calpastatin proteins of the present invention can be extracted and purified from the recombinant host by using known protein purification techniques commonly employed, such as extraction, precipitation, ion exchange chromatography, affinity chromatography, gel filtration and the like. Biochemical techniques employed to isolate the calpastatin proteins of the present invention from neural tissue are of particular interest when purifying these proteins from a recombinant host.

F. Detection of Calpastatin Proteins

The present invention also includes methods of detecting HMWC and LMWC or their functional derivatives in a sample or subject. The calpastatin proteins of the present invention may be detected with any appropriate ligand, for example, an antibody which is detectably labeled. Illustrative labels include radioisotope, fluorescent, chemiluminescent, enzyme labels and the like. Methods of detecting such detectably labeled antibodies are well known to those of ordinary skill in the art and may be performed in vitro or in vivo. For example, in vivo imaging assays as described by Goldenberg et al., U.S. Pat. No. 4,444,744 (herein incorporated by reference) may be used.

Once the calpastatins are isolated and purified, these proteins and their immunogenic fragments can be used as antigens to raise antibodies specific for the calpastatins. Methods for producing monoclonal, polyclonal, and region-specific antibodies are known to one of skill in the art. Techniques for preparing antibodies, labeling antibodies, and performing. immunoassays are described by Harlow et al. In: *Antibodies, A Laboratory Manual* (supra).

In addition, the materials for use in the assay of the invention are ideally suited for preparation of a kit. Such a kit may comprise in close confinement one or more container means such as vials, test tubes, and the like. Each of said container means comprises one of the separate elements to be used in the assay method.

For example, one of said container means may comprise antibodies directed against one or more calpastatin proteins. Such antibodies may be bound to a separate solid phase immunoabsorbent or directly to the inner walls of a container. The carrier may also contain, in addition, a plurality of containers each of which comprises different, predetermined and known amounts of antigen. These latter containers can then be used to prepare a standard curve from which can be interpolated the results obtained from the sample containing the unknown amount of antigen.

Antibodies to the HMW calpastatin, described by this invention, recognized abnormalities associated with Alzheimer's disease and Down's syndrome. A down-regulation of CANP by an overabundance or redistribution of its inhibitors represents a reasonable and testable mechanism to account for the accumulation and/or abnormal processing of intracellular cytoskeletal proteins.

Understanding of the endogenous inhibitors of CANP activity in human brain, and an ability to manipulate them, would enable the modification or alteration of the mechanisms of atrophy and neuronal death in human brain, the products of neuronal degeneration, and therefore, the processes of pathological neurodegenerative disease, such as Alzheimer's Disease (AD).

G. Uses of Calpastatin Proteins

Since antibodies to the calpastatins recognize abnormalities in Alzheimer's Disease (AD) brain, as well as other as yet uncharacterized intraneuronal lesions, such antibodies would be useful in establishing the pathological diagnosis of AD. If they recognize an early event in the sequence of pathogenetic events leading to the death of the neuron in this and other neurofibrillary diseases, antibodies to the calpastatin proteins of the present invention would be useful markers in the experimental studies on mechanisms related to AD pathogenesis (i.e., investigational tools).

Antibodies to the entire molecule or part of the molecule may be used therapeutically to modulate calcium-activated proteolysis in various parts of the body. For example, calcium-activated proteolysis may be involved in various aspects of platelet functions, including clotting mechanisms (Noszek et al., *Soc. Neurosci. Abstr.* 13:1684 (1987); Moreau et al., *Eur. J. Biochem.* 173:185–190 (1988)) and may alter the function of leucocytes, including their release of materials into the extracellular environment (Pontremoli et al., *J. Biol. Chem.* 263:1915–1919 (1988)). Therefore, direct application of antibodies could have effects of potential clinical relevance on extracellular processes, such as blood coagulation, inflammatory responses as occur in arthritis, for example, infectious processes, and uncontrolled cell growth processes such as cancer. In fact, inhibitors of CANP appear to have significant effects in slowing the growth of certain cancers (Shoji-Kasai et al., *Proc. Natl. Acad. Sci., USA* 85:146-150 (1988)).

The direct use of the calpastatin molecule or a modified form with slower metabolism or greater accessibility to particular cellular compartments (or the use of anti-calpastatin antibodies) may have potential use in these disease states. In spinal cord trauma and other forms of neural cell injury, CANPs are abnormally activated and synthetic CANP inhibitors (that also inhibit other proteinases) reduce the cell damage (Siman et al., *Soc. Neurosci. Abstr.* 13:1684 (1987)). Since calpastatins are the only known specific inhibitors of CANP, these polypeptides (or derivatives of them based on their structure) may have greater therapeutic benefit without causing cellular toxicity by inhibiting other processes. These calpastatin polypeptides may also be useful as a basis for designing molecules that have cellular specificity in modulating CANPs.

Cell death induced by ischemia or excitations has been implicated in several disease states including Huntington's disease, Parkinson's disease, Alzheimer's Disease, etc. In each of these cases, recent data indicate that CANPs are abnormally activated. Inhibitors of CANP such as HMWC and LMWC may therefore be useful in these conditions.

With these considerations as background, if calpastatin is structurally or functionally abnormal in Alzheimer's Disease in a way that is important to the pathogenesis of AD, calpastatins have the following potential utility. The availability of the protein would be essential to the development of drugs aimed at modifying the interaction of calpastatin with CANP (depending on the situation, enhancing or inhibiting calpastatin function). The availability of calpastatin molecules in purified form, and antibodies thereto as described herein, enables the development of compounds modeled after the structure of this molecule or a domain of the polypeptide. Antibodies to these polypeptides would be potentially useful in diagnostic applications since antibodies to high molecular weight calpastatin recognize pathological stuctures associated with AD. The polypeptides, or some derivative domain, could be useful in the treatment of conditions in which CANP activity may be abnormally increased, e.g., ischemia and cytotoxin-mediated cell death, to limit cell death due to metabolic or traumatic insults.

Having now generally described the invention, the same will be more readily understood through reference to the following examples which are provided by way of illustration, and are not intended to be limiting of the present invention, unless specified. All references described in the specification are herein incorporated by reference in their entirety.

EXAMPLES

In the examples that follow, the materials and reagents were obtained from the sources indicated.

Calpastatin was prepared from postmortem human brain provided by Dr. Edward Bird from the McLean Hospital Brain Tissue Resource Center (Belmont, Mass., U.S.A.); azocasein was obtained from Sigma Chemical Co. (St. Louis, Miss., U.S.A.); $^{14}$C-formaldehyde (specific activity 47 uCi/mmol) was purchased from New England Nuclear Corp. (Boston, Mass., U.S.A.); diethylaminoethyl (DEAE)-cellulose (DE-52) was purchased from Whatman BioSystems Ltd. (Maidstone, Kent, England); DEAE-Sepharose CL-4B and Sephacryl-300 was purchased from Pharmacia, Inc. (Piscataway, N.J., U.S.A.); Ultrogel AcA-44 and Ultrogel AcA34 was purchased from IBF Biotechnics, Inc. (Savage, Md.); acrylamide and molecular weight proteins were purchased from BioRad Laboratories (Richmond, Calif., U.S.A.); nitrocellulose membrane and horseradish peroxidase (HRP)-conjugated goat anti-rabbit IgG are products of Millipore Corp. (Bedford, Mass., U.S.A.) and Cappell Laboratories (Cochranville, Pa., U.S.A.), respectively. Polyvinylidene difluoride (PVDF)-membrane (Immobilon-P) was purchased from Millipore Corporation (Bedford, Mass.). Peroxidase-labeled sheep anti-rabbit IgG was the product of Kirkegard and Perry Laboratories, Inc. (Gaithersburg, Md.). Other chemicals were reagent grade.

The following buffers were used in the chromatographic and assay procedures: Buffer A: 20 mM Tris-HCl (pH 7.4), 1 mM EGTA, 2 mM EDTA, 0.5 mM dithiothreitol (DTT), 1 mM benzamidine, 0.004% NAN$_3$, and 0.15M KCl; Buffer B: 50 mM Tris-HCl (pH 7.4), 5 mM EDTA, 2 mM EGTA, 5 mM DTT, 2 mM benzamidine, 0.2 mM aprotinin, and 1 mM PMSF; Buffer C: 20 mM Tris-HCl (pH 7.4), 0.15M KCl, 2 mM EDTA, 1 mM EGTA, 0.5 mM DTT, 1 mM benzamidine and 0.004% NAN$_3$; and Buffer D: 20 mM Tris-HCl (pH 7.4), 1 mM EGTA, 2 mM EDTA, 1 mM DTT, 1 mM benzamidine. CANP assays were performed in 100 mM Tris (pH 7.4) and 2 mM DTT (Buffer E). The buffer used for the SDS Polyacrylamide Gel Electrophoresis was Buffer G: 25 mM Tris base, 192 mM Glycine, 0.1% SDS; and the buffer used for the transblotting apparatus was Buffer H: 25 mM Tris base, 192 mM Glycine, 15% Methanol.

Isolation and Purification of HMW and LMW Calpastatin

Human cerebral cortex, including gray and white matter, was dissected from brains of individuals without a history of neuropsychiatric disease and which exhibited no gross histological abnormalities. The postmortem interval before freezing at −20° C. was 8–20 hours for all samples. The brains were subsequently stored for one month to 1.5 years at −70° C. before analysis.

Anion Exchange on DEAE Cellulose:

Human cerebral cortical tissue (200–1200 g) was homogenized in four volumes of cold buffer B. All subsequent steps were performed at 0°–4° C. After centrifugation at 16,000× g, the protein was concentrated by precipitation in 35–65% ammonium sulfate. The precipitate was collected by centrifugation and resuspended in 4 volumes of buffer B with gentle shaking. This solution was dialyzed against buffer B for 48 hours and then applied to a 4.4×30 cm column of DEAE-cellulose (DE-52) equilibrated with buffer B. After extensive washing, the column was eluted with a 4000 ml KCl gradient (0–0.4M) in buffer B at a flow rate of 100 ml/hr.; 15 ml fractions were collected. Fractions containing inhibitor activity were pooled and the protein was concentrated by ammonium sulfate precipitation between 35–65% ammonium sulfate as described above.

Gel Chromatography on Ultrogel AcA44:

The calpastatin fractions in the previous stage (DEAE-cellulose) were applied to a column (4.4×90 cm) of Ultrogel AcA44 equilibrated with buffer C. The column was eluted with the above buffer at a flow-rate of 35 ml/hr and 13 ml fractions were collected in each tube. Two CANP inhibitory activities were eluted from the Ultrogel AcA44 column. The inhibitor fractions having an inhibitory activity greater than 50% were combined as Fraction I (HMWC) and Fraction II (LMWC), from earlier and later inhibitory peaks, respectively. Fraction I (HMWC) was dialyzed against buffer D at 0° C.

DEAE-Sepharose CL 4B Chromatography:

The dialyzate (HMWC) from the previous step (Ultrogel AcA44) was applied to a column (2.5×25 cm) of DEAE-Sepharose CL 4B equilibrated with buffer D. After the column was washed with 800 ml of buffer D, the column was eluted with a linear gradient of 0–0.4M KCl (total 700 ml) in buffer D. The flow rate was 50 ml/hr, and 10 ml fractions were collected. The inhibitor fractions eluted with KCl gradient were pooled and concentrated with the aid of Centriprep-10 (Amicon Corp.).

Ions-exchange chromatography with CM cellulose:

The pooled fractions of LMWC obtained from Ultrogel AcA-44 column were purified over a CM-cellulose ion-exchange column at pH 5.0. Pooled LMWC was dialyzed against 20 mM Na-acetate, pH 5.0, 1 mM GGTA, 2 mM EDTA, 2 mM benzamidine at 0° C. The dialyzate was applied to a column (2.5×25 cm) of CM-cellulose (CM-52, Whitman) equilibrated with buffer E. After the column was washed with 800 ml of buffer E, the column was eluted with a linear gradient of 0–0.4M NaCl (total 700 ml) in buffer E. The flow rate was 50 ml/hr, and 10 ml fractions were collected. The inhibitor fractions were pooled and concentrated with the aid of Centriprep-10 (Amicon Corp.).

Affinity Chromatography of LMWC on Con A-Sepharose:

The inhibitor fractions from CM-cellulose were pooled and concentrated for the next purification step. The concentrated sample was loaded to a column (1.5×5 cm) of Con A-Sepharose equilibrated with 20 mM Tris-HCl, pH 7.4, 1 mM benzamidine and 0.5M NaCl. After the column was washed extensively with the buffer, the column was eluted with 0.5M methyl α-D-glucopyranoside in 20 mM Tris-HCl, pH 7.4 and 1 mM benzamidine. The LMWC was recovered in the non-binding fraction whereas α PI was separated from LMWC into the binding fraction.

Heat treatment:

The HMWC inhibitor obtained from the DEAE-Sepharose CL-4B column was heated at 100° C. for 5 min, cooled to 0° C., and centrifuged at 100,000×g for 30 min at 4° C.

The LMWC inhibitor obtained from the Con A-Sepharose column was heat treated as above.

Gel chromatography:

After heat treatment, the HMWC supernatant from the heat treatment step was applied to a column (2.5×115 cm) of Ultrogel AcA34 equilibrated with buffer C. A flow rate of 23.0 ml/hr was used and 5 ml fractions were collected in each tube. In contrast, the heat treated supernatant containing LMWC was applied to a Sephacryl S-300 column (2.5×120 cm) equilibrated with buffer C. The column was run with a flow rate of 12.5 ml/hr and 5 ml fractions were collected.

II. Assay of Protein Concentration and Inhibitor Activity

[$^{14}$C]-azocasein was prepared by reductive alkylation with [$^{14}$C]-formaldehyde (Dottavio-Martin et al., *Anal. Biochem.* 87:562–565 (1978)). Calpastatin activity was expressed in terms of ability to decrease the activity of human brain CANP. Millimolar calcium-dependent proteinase was purified to homogeneity from postmortem human brain as previously described (Vitto et al. *J. Neurochem.* 47:1039–1051 (1986). Fractions containing inhibitor activity were pre-incubated with mCANP. After a 10-min preincubation at 4° C. the reaction was initiated by the addition of calcium chloride in a reaction mixture containing 50 mM Tris-HCl (pH 7.4), 5 mM CaCl$_2$, 1 mM DTT, 0.25% (W/V) azocasein plus [$^{14}$C]-azocasein (specific activity: 133 cpm/ug [$^{14}$C-azocasein]). After incubation for 30 min at 30° C., the reaction was terminated with 300 μL of cold 10% trichloroacetic acid. Enzyme activity was measured as the radioactivity in the acid-soluble fraction after centrifugation as previously described (Nixon, *Brain Res.* 200:69–83 (1980)). Acid-soluble radioactivity was determined in samples lacking enzyme, and this value was subtracted from the experimental samples as non-enzymatic "background." In the absence of inhibitor, the rate of azocasein hydrolysis was constant during 30 min of incubation and increased in proportion to the amount of enzyme protein. Specific calcium-dependent proteinase inhibitor activity was calculated from curves describing the inhibition of CANP activity with increasing amounts of inhibitor protein. One unit of inhibitor activity was defined as the amount of protein required to inhibit 50% of the activity of 0.5 mg of purified CANP. In cases where the presence of inhibitor but not its specific activity was required, inhibitory activity was measuring using a human brain mCANP fraction partially purified by DE-52 chromatography (Vitto et al. *J. Neurochem.* 47:1039–1051 (1986)). The amount of proteinase inhibitor added to the assay was adjusted to yield approximately 50% inhibition of CANP.

III. Additional Methods

Estimation of Molecular Weight of Calpastatin on Ultrogel AcA34

The native molecular weight of calpastatin was estimated on a column (2.5×115 cm) of Ultrogel AcA34. The column was pre-equilibrated and eluted with buffer C at a flow rate of 23 ml/hr. Fractions of 5 ml were collected in each tube. The following protein standards were used to determine the molecular weight of calpastatin proteins: Catalase ($M_r$=240,000), aldolase ($M_r$=158,000), bovine serum albumin ($M_r$=68,000), ovalbumin ($M_r$=45,000), chymotrypsinogen A ($M_r$=25,000), and ferritin (450,000).

Estimation of Molecular Weight of Calpastatin on Sephacryl S-300

The native molecular weight of calpastatin (LMWC) was examined on a column (2.5×120 cm) of Sephacryl S-300. The column was pre-equilibrated and eluted with buffer C at a flow rate of 15 ml/hr. Fractions of 5 ml were collected in each tube. The molecular weight was determined by using following standards, Aldolase ($M_r$=158,000), bovine serum albumin (68,000), ovalbumin (45,000), and chymotrypsinogen A ($M_r$=25,000).

Polyacrylamide Gel Electrophoresis

Samples were analyzed by electrophoresis in sodium dodecylsulfate-polyacrylamide (SDS-PAGE) slab gels by the method of Laemmli (*Nature* 227:680–685 (1970)). The standard proteins, phosphorylase b, bovine serum albumin, ovalbumin, carbonic anhydrase, soybean trypsin inhibitor, and lysozyme of molecular weights 92,500, 68,000, 45,000, 31,000, 21,500, and 14,400, respectively, were used.

Two-dimensional Gel Electrophoresis

Two-dimensional gel electrophoresis was performed according to O'Farrell (*J. Biol. Chem.* 250:4007–4027 (1975)). Gels were stained for proteins with Coomassie Blue, or proteins from gels were electrophoretically transferred to PVDF-membranes or nitrocellulose membranes and immunostained with affinity purified antibody (I-2-7) to the high molecular weight calpastatin.

Isoelectric Focusing of Purified Calpastatins

Purified calpastatins were subjected to isoelectric focusing in 6.5% polyacrylamide gel containing 2.5% ampholine (pH 3–8), 1.6M urea, and 0.5% NP-40 at 4° C. The gels were sliced into 3 mm segments, and each segment was assayed for calpastatin by the standard assay protocol.

Amino Acid Analysis and Protein Sequencing

High molecular weight and low molecular weight calpastatins were purified as demonstrated in FIGS. 1 and 2. Aliquots of each purified fraction were subjected to SDS-polyacrylamide gel electrophoresis (10% polyacrylamide gel containing 0.1% SDS in Laemmli's system (*Nature* 227:680–685 (1970)). Proteins on the gels were electrophoretically transferred to PVDF (polyvinylidine difluoride)- membrane (Immobilon-P) in 10% methanol CAPS (3-(cyclohexylamino)-1-propanesulfonic acid) buffer (pH 11.0) system. The proteins were identified on the membrane by staining with Coomassie Brilliant Blue R. The appropriate bands were excised from the membranes and subjected to amino acid analysis and sequence analysis (Matsudaira, *J. Biol. Chem.* 262:10035–10038 (1987)). Automated Edman degradation was performed on an Applied Biosystems Model 470-AA gas liquid-phase protein sequencer. PTH-amino acids recovered at each cycle of the Edman degradation were analyzed equipped on-line with an Applied Biosystems Model 120-A HPLC.

Immunoblotting

Immunoblotting was performed according to Towbin et al. (*Proc. Natl. Acad. Sci. USA* 76:4350–4354, 1979) in transfer buffer containing 15% MeOH, 25 mM Tris, and 192 mM glycine (pH 8.3) by applying constant current (0.5 A) at 2° C. Proteins were electrophoretically transferred onto PVDF-membrane or nitrocellulose-membrane. Non-specific background was removed by incubating the membrane with 20 mM Tris-HCl (pH 7.4), plus 0.5M NaCl and 5% non-fat dried milk blocking solution for 1 hr at room temperature. Purified sheep IgG (1 mg/ml) to human brain HMWC calpastatin (I-2-7) was diluted 1:10–1:1000 in blocking buffer and incubated with the transfer membrane overnight at 4° C. Peroxidase-conjugated rabbit anti-sheep IgG was diluted 1:1000 (stock sol. of 1 mg IgG/ml) in blocking solution and membranes were incubated for 5 hr at room temperature. After several washes of the membranes with TBS, peroxidase activity was visualized with $H_2O_2$ and 0.001% 4-chloro-1-naphthol plus N,N'-dimethyl-p-phenylenediamine according to the method developed by Kobayashi and Tashima (*Anal. Biochem.* 183:9–12 (1989)).

Immunocytochemistry

Postmortem human brains from individuals with Alzheimer's disease (AD) and age-matched (62 to 78 years) neurologically normal brains were used in this study. CNS tissue was procured from the McLean Hospital Brain Tissue Resource Center (Belmont, Mass.) and Massachusetts General Hospital (Boston, Mass.). Premortem clinical diagnosis of Alzheimer's disease was confirmed neuropathologically. Control brains were obtained from individuals with no history of neuropsychiatric disease and exhibited no gross or microscopic histopathology. The postmortem interval before immersion fixation in 10% phosphate-buffered formalin for all specimens used in this study was 12 to 24 hours.

Tissue blocks (3×1×0.4 cm) from the prefrontal cortex of fixed brains were cut into 30 to 35 μ-thick sections using a Lancer Series 1000 vibratome. Brain sections were treated with Nissl and/or Bielshowsky stains for routine histological inspection or were processed for immunocytochemistry. Additional vibratome sections were immunostained using a rhodamine-conjugated goat-anti rabbit secondary antibody and/or stained with thioflavin S (Cappel/Worthington Biochemicals, Cooper Biomedials, Malvern, Pa.) to verify the presence or absence of paired helical filaments or senile plaques.

For histological demonstration of anti-calpastatin immunoreactivities, a modification of the avidin-biotin complex (ABC) method of Hsu et al. (*J. Histochem. Cytochem.* 29:577–580 (1981)) was employed as follows: 1) free-floating sections were incubated for 30 minutes at room temperature in $CH_3OH$ with 0.3% $H_2O_2$; 2) sections were washed 3 times for 10 minutes each in "diluting solution" which consisted of 20 mM Tris-buffered saline (TBS)-pH 7.4, 0.4% Triton X-100, 2% bovine serum albumin (BSA), 1% normal goat or rabbit serum, and 0.9% NaCl; 3) tissue sections were blocked for 30 minutes at room temperature with 20% normal goat or rabbit serum in 20 mM TBS; after blocking, sections were incubated from 12–72 hours at 4° C.

in anti-calpastatin antisera using dilutions of 1:250–1:1000. Serial dilutions of antisera were made in "diluting fluid"; 5) sections were washed 3 times for 10 minutes each in diluting fluid; 6) following incubation in primary antisera, sections were incubated for 30 minutes at room temperature in 20 mM TBS-biotinylated secondary antibody (either biotinylated goat anti-rabbit or rabbit anti-sheep), 45 microliters/10 cc) in 20 mM TBS); 7) sections were washed 3 times for 10 minutes each in diluting fluid and subsequently incubated for 60 minutes at room temperature in avidin (90 microliters/10 cc)-biotin (90 microliters/10 cc) in 20 mM TBS); sections were washed 3 times in diluting solution. All biotinylated secondary antibodies and avidin-biotin reagents were obtained from Vector Laboratories, Inc., Burlingame, Calif. Following washes, tissue sections were incubated for 5 minutes in diaminobenzidine (1 mg/ml) in 10 mM TBS-0.02% $H_2O_2$ at room temperature; sections were washed 3–5 minutes in distilled water and rinsed 1–3 minutes in 20 mM TBS.

IV. Results of Purification and Characterization

Purification of HMWC and LMWC Calpastatin

Table 1 summarizes the purification data of HMW human brain calpastatin (41 Kda calpastatin). More than 19% of the inhibitory activity was recovered and the 41 Kda calpastatin was purified 964-fold over the DEAE-cellulose partially purified inhibitor. The final specific activity of purified material was approximately 36,000 units/mg protein. As seen in Table 1, heat-treatment and Ultrogel AcA34 steps were very effective for the purification and increased the purification in each step more than 24-fold and 22-fold, respectively.

Figure 3:
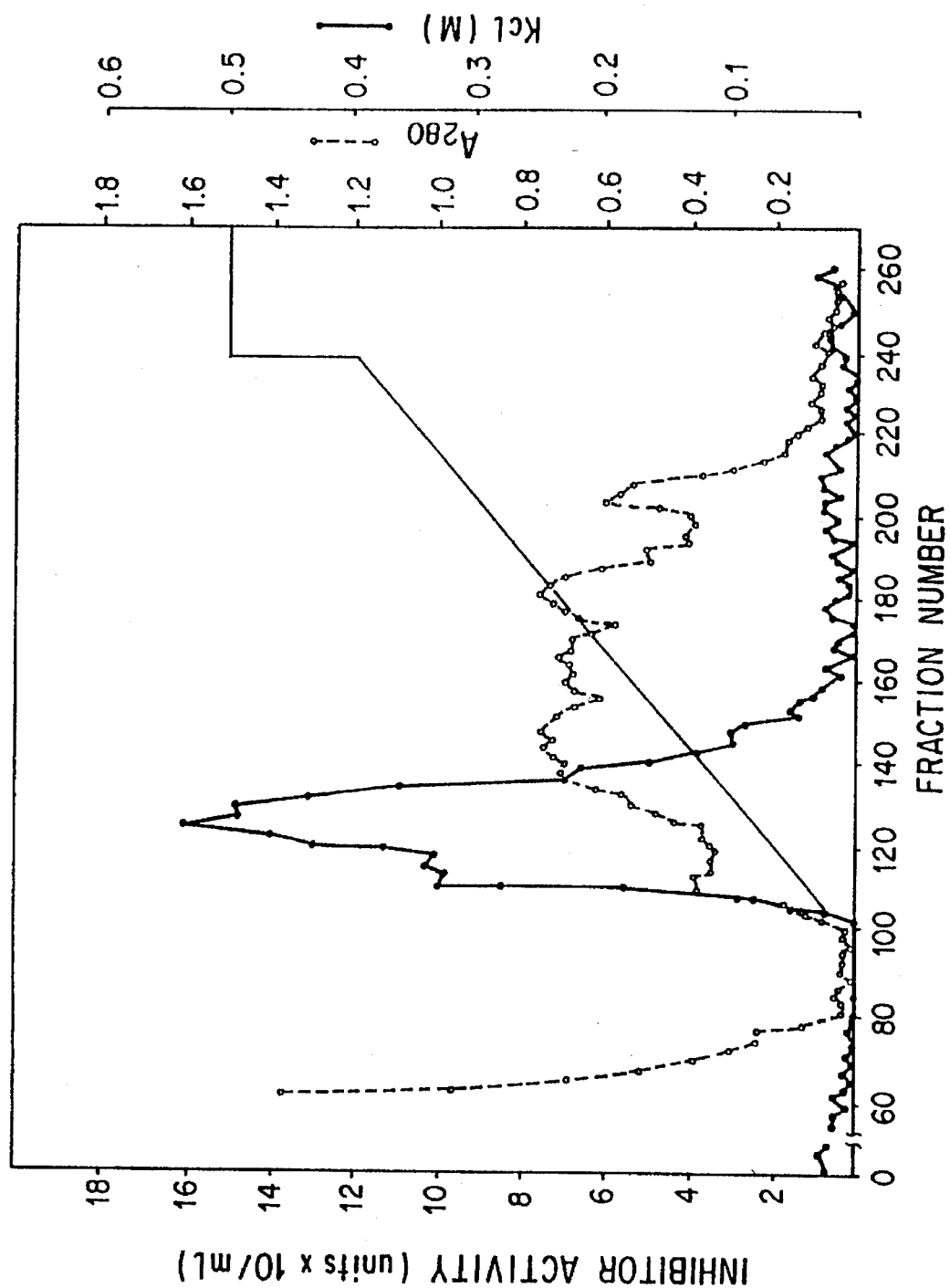
FIG. 3. Ion exchange chromatography of calpastatin from human cerebral cortex: Proteinase inhibitory activity (closed circles) and absorbance at 280 nm (open circles). Chromatography of a 30,000 g supernatant extract of brain was carried out on DEAE-cellulose (see Examples section). Enzyme activity was eluted with a 0–0.4M linear gradient of KCl. Aliquots of each fraction were assayed for CANP inhibitory activity as described in the Examples section.

Although some calpastatin activity is detectable in the crude homogenate, a fair amount of endogenous calpain activity disturbs an accurate determination of inhibitory activity. We therefore introduced ion-exchange chromatography on DEAE-cellulose (DE-52) to separate calpain and calpastatin. The column was eluted with a linear salt gradient (FIG. 3). Inhibitory activity was eluted at a salt concentration between 0.05 and 0.15M KCl from the column as a single peak of activity. The mCANP was eluted at 0.25–0.3M KCl in a separated fraction from calpastatin.

Figure 4:
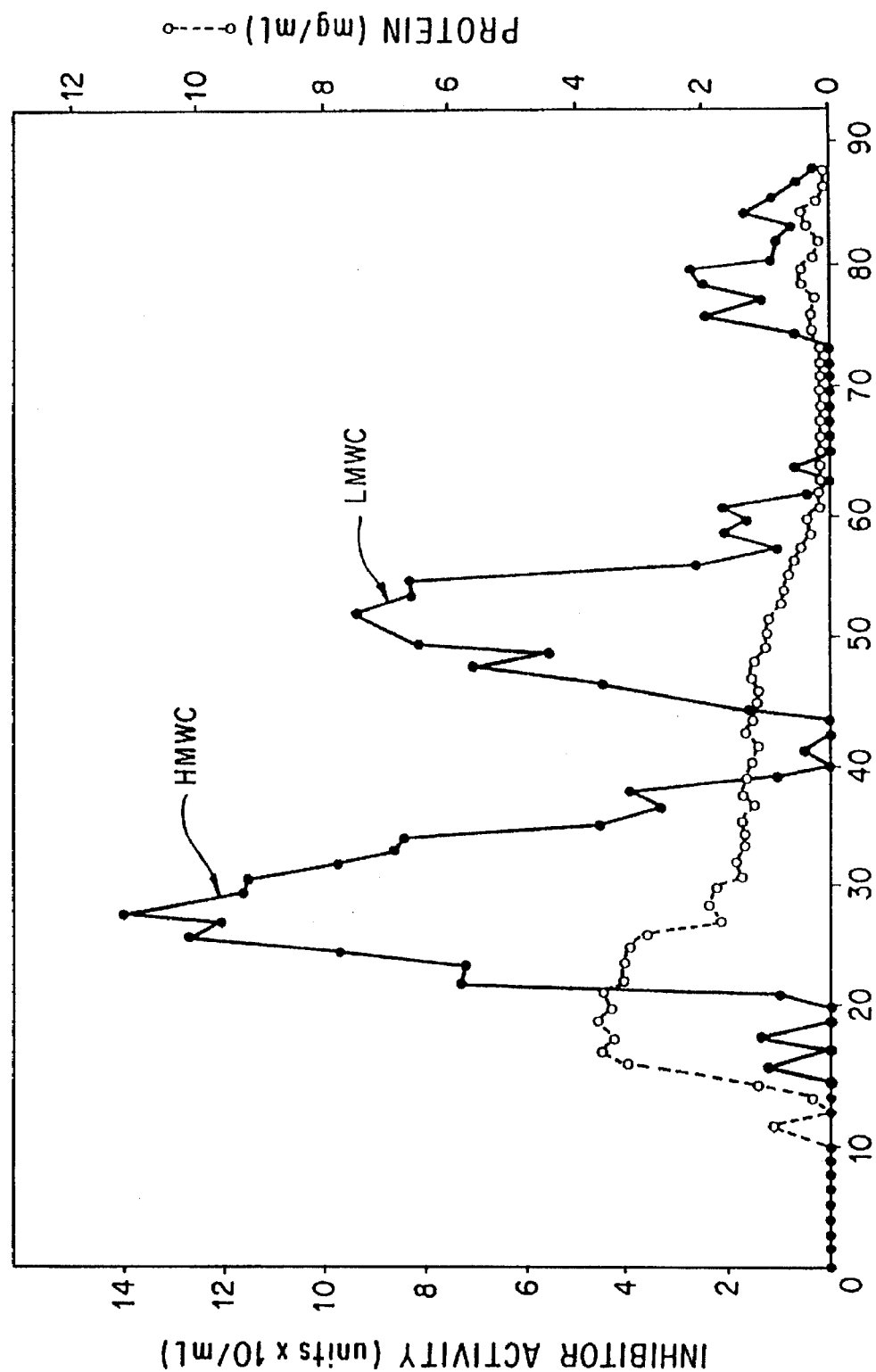
FIG. 4. Gel filtration chromatography of DEAE-cellulose purified calpastatin: CANP inhibitory activity (closed circles) and relative protein concentration (open circles) determined by the method of Bradford, M. M., Anal. Biochem., 72:248–254 (1976). The active fractions from FIG. 3 were concentrated by ammonium sulfate precipitation and applied to a column of Ultrogel AcA-44 which was eluted as described in the Examples section. The active fractions subjected to further purification are indicated. Peaks of inhibitory activity corresponding to HMWC and LMWC are indicated in the figure.

The pooled calpastatin fraction after DEAE-cellulose chromatography was applied to further purification on Ultrogel AcA44 column chromatography. FIG. 4 shows a typical elution profile of DEAE-cellulose fraction on Ultrogel AcA44 and demonstrates that calpastatin(s) is eluted as two peaks of inhibitory activity (fraction U-1, and U-2. The earliest eluting peak (U-1) corresponding to HMWC contained approximately 60% of the total activity. The second peak of activity (U-2) corresponding to LMWC contained about 40% of the total inhibitory activity. Purification and characterization of these fractions (U1 and U2) is discussed below.

TABLE 1

Purification of High Molecular Weight Calpastatin from Human Brain

| Purification Stage | Volume (ml) | Total Activity (Units)* × 10–3 | Total Protein (mg) | Yield (%) | Specific Activity (units/mg) | Purification (–fold) |
|---|---|---|---|---|---|---|
| Human Brain Homogenate | 3600 | | | | | |
| DEAE-cellulose Pooled Fraction (DE-I) | 1080 | 55.0 | 1500 | 100 | 37 | 1 |
| Ultrogel AcA 44 Fraction I (U-1) | 230 | 25.3 | 550 | 46 | 46 | 1.2 |
| DEAE-Sepharose CL4B | 80 | 18.6 | 282 | 34 | 66 | 1.8 |
| Heat-treatment (100° C., 5 min) 100,000 × g Supernatant | 8 | 18.0 | 11.3 | 33 | 1593 | 43.1 |
| Ultrogel AcA 34 | 15 | 10.7 | 0.3 | 19.5 | 35667 | 964 |

*One unit of inhibitor activity was defined as the inhibition of 50% of the activity of 0.5 µg of CANP.

a. Purification of HMWC

The active fractions of U-1 were pooled, dialyzed and applied to the second ion-exchange chromatography on DEAE-Sepharose CL 4B which was eluted with a linear gradient of KCl. Inhibitory activity elutes with that position of the gradient at a salt concentration between 0.15 and 0.23 from this column.

Figure 6:
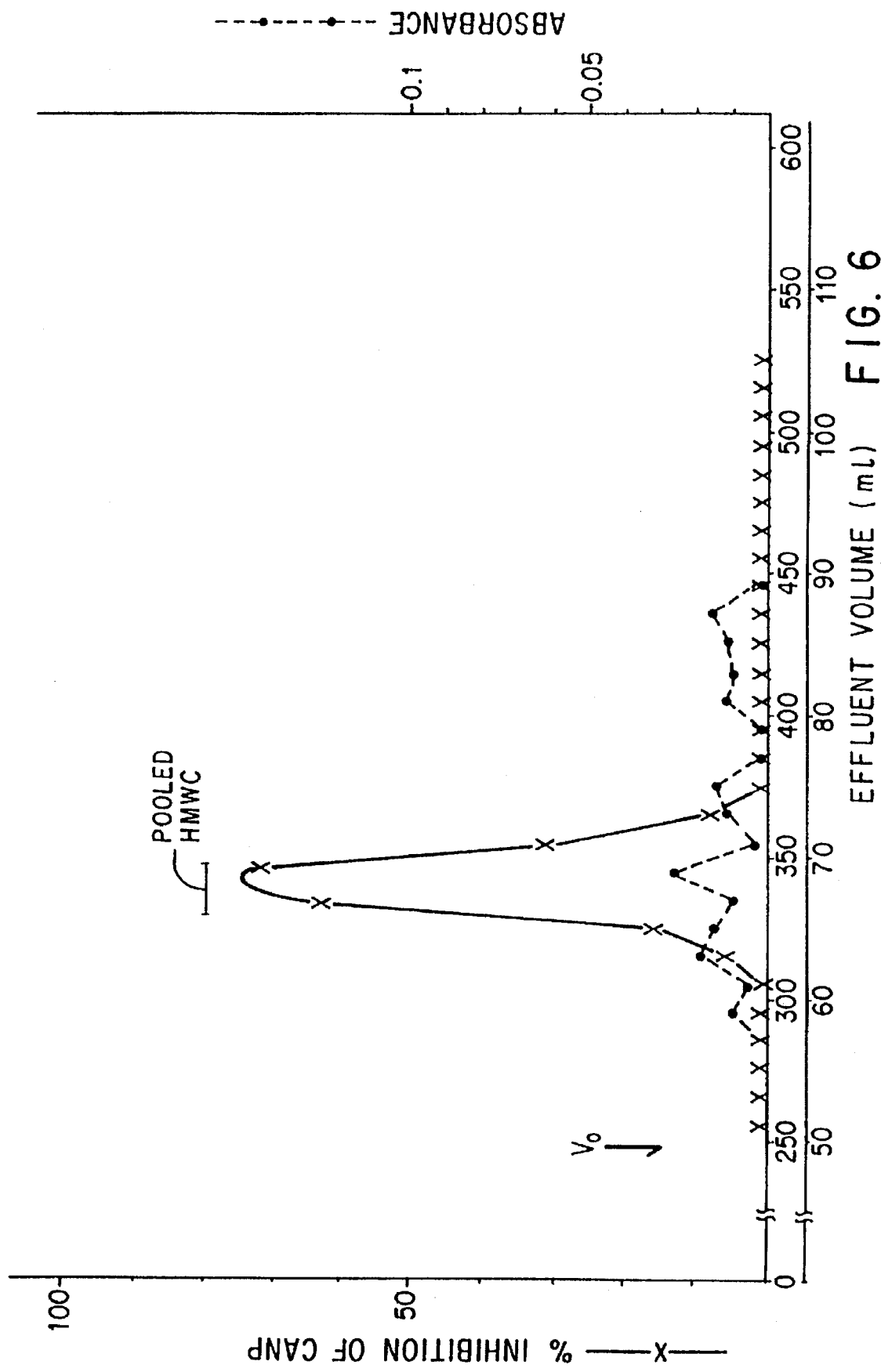
FIG. 6. Gel chromatography of HMWC from human brain on Ultrogel AcA34. HMWC from DEAE-Sepharose fraction was heated at 100° C. for 5 min. Heat-treated HMWC fraction was centrifuged at 100,000×g for 30 min. The supernatant was recovered and applied to a column (2.5×115 cm) of Ultrogel AcA34. Five ml fractions were collected and assayed for their ability to inhibit mCANP. The elution positions of standard proteins (Ferritin, 450 kDa; Catalese, 240 kDa; aldolase, 160 kDa; and bovine serum albumin, 68 kDa) were determined in separate experiments.

The pooled inhibitor fraction after DEAE-Sepharose CL-4B chromatography was heat-treated at 100° C. for 5 min. The boiled fraction was centrifuged at 100,000×g for 30 minutes and the supernatant was recovered as inhibitor fraction. Interestingly, more than 95% of contaminated protein was removed by this treatment, and 100% of inhibitory activity was recovered in the supernatant. The heated fraction was further analyzed on Ultrogel AcA34 column chromatography. The inhibitory activity was recovered as a single symmetrical peak from this column at the position of 300 kDa protein (FIG. 6). The molecular size of 300 kDa did not change with or without heat-treatment of this fraction on Ultrogel AcA34 under a non-denaturing condition.

b. Purification of LMWC

Figure 11:
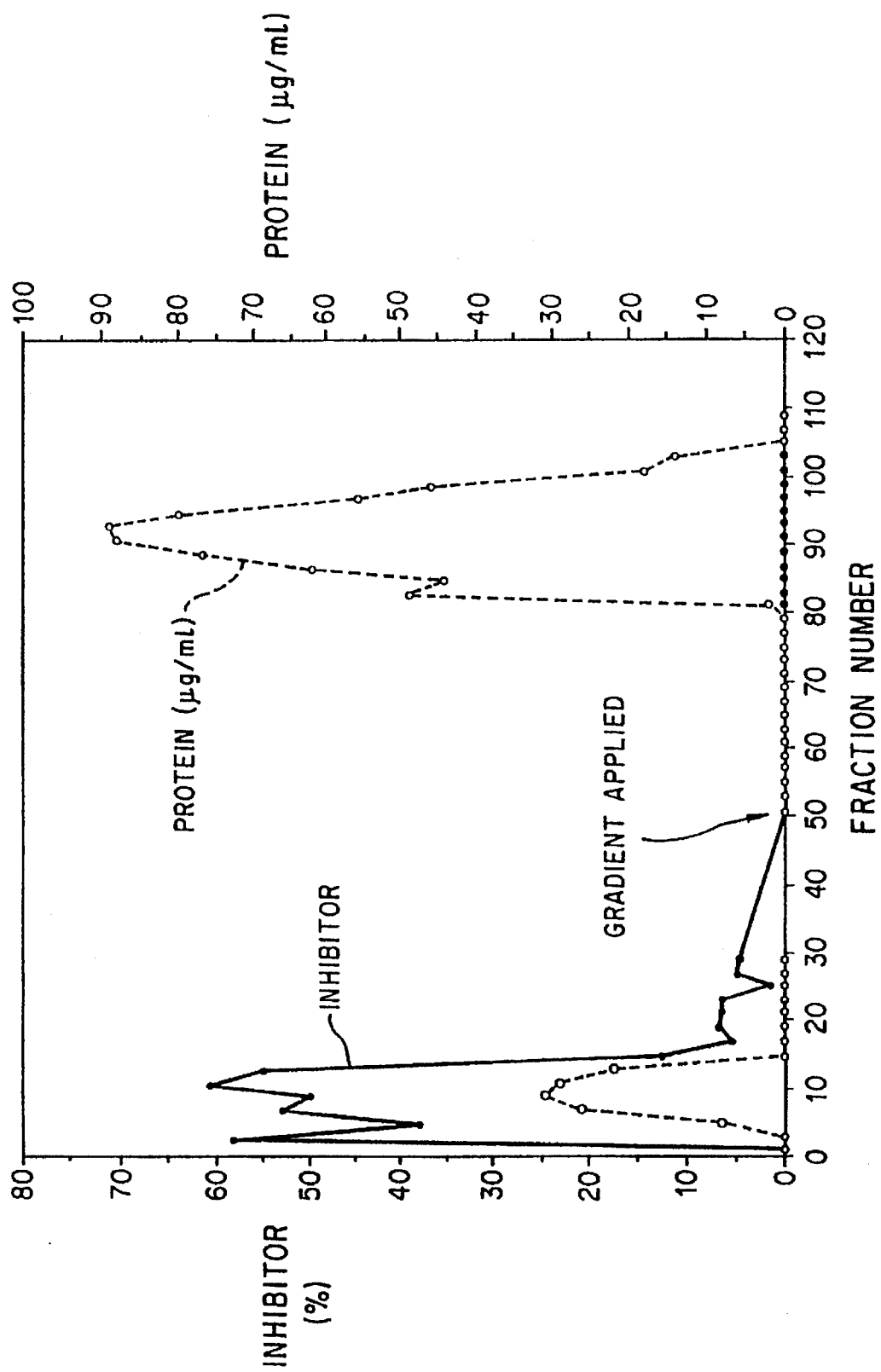
FIG. 11. Ion-exchange chromatography with CM cellulose: The pooled fractions of LMWC obtained from Ultrogel AcA-44 column were purified over a CM-cellulose ion-exchange column at pH 5.0. LMWC was dialyzed against 20 mM Na-acetate, pH 5.0, 1 mM EGTA, 2 mM EDTA, 1 mM DTT, 1 mM benzamidine at 0° C. The dialyzate was applied to a column (2.5×25 cm) of CM-cellulose (CM-52, Whatman) equilibrated with buffer E. After the column was washed with 800 ml of buffer E, the column was eluted with a linear gradient of 0–0.4M NaCl (total 700 ml) in buffer E. The flow rate was 50 ml/hr, and 10 ml fractions were collected. The inhibitor fractions were pooled and concentrated with the aid of Centriprep-10 (Amicon Corp.).
Figure 12:
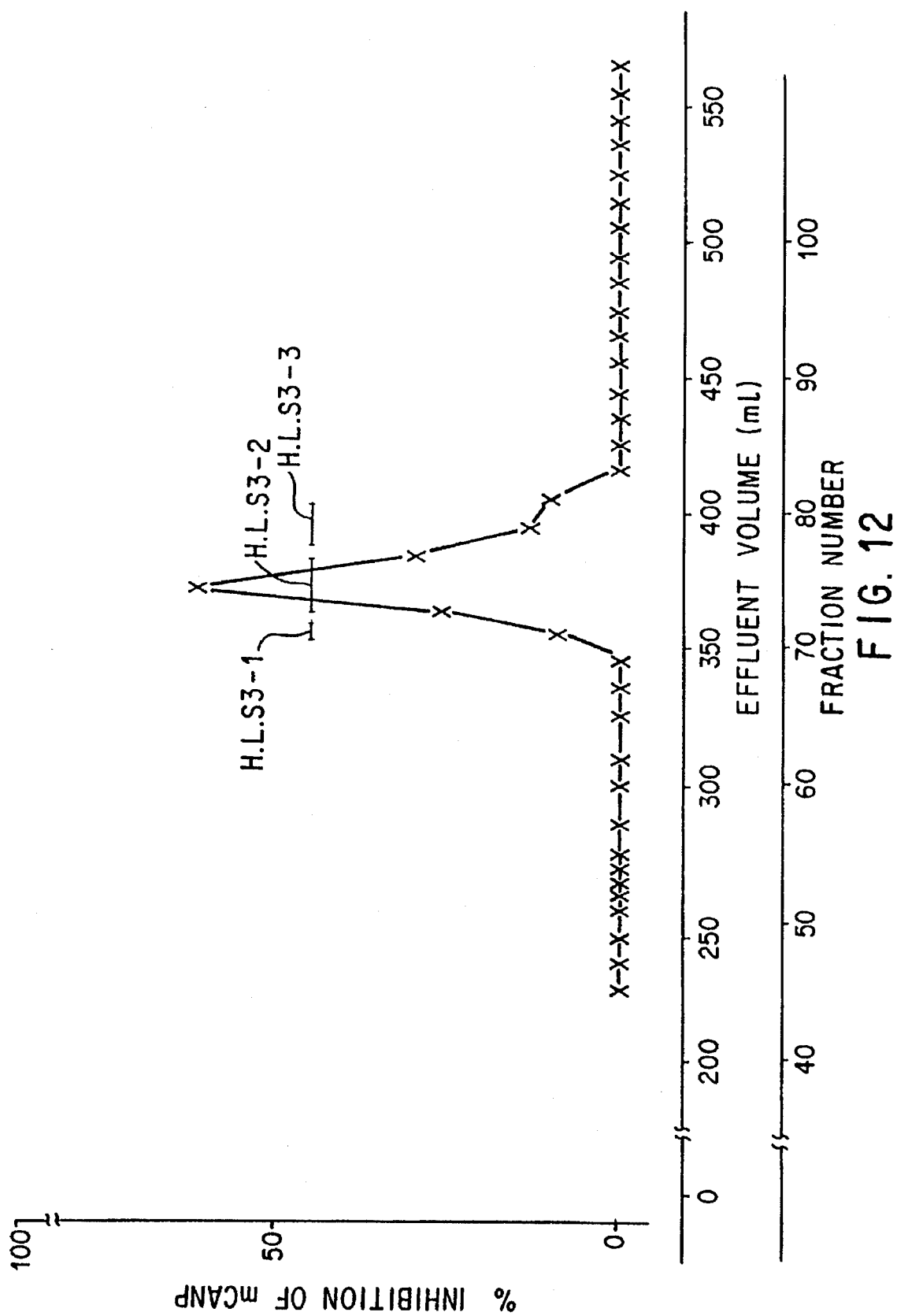
FIG. 12. Gel chromatography of LMWC from human brain on Sephacryl S-300. The supernatant of heat-treated partially purified LMWC was applied to Sephacryl S-300. The column was eluted with 20 mM Tris-HCl, pH 7.4, 0.15M KCl, 0.5 mM DTT, 2 mM EDTA, 1 mMEDTA, 1 mM EGTA, 1 mM benzamidine and 0.004% NaN$_3$ and 5 ml of fractions was collected. Each fraction was assayed for the inhibition of mCANP. The elution positions of standard proteins (Aldolase, 160 kDa; bovine serum albumin, 68 kDa; ovalbumin, 45 kDa; and chymotryposinogen A, 25 kDa) were determined in separate experiments.

The U-2 active fraction corresponding to LMWC was subjected to ion-exchange chromatography on CM cellulose (CM-52) (FIG. 11). The inhibitor assay and protein determination profiles of the eluted fractions from CM-cellulose demonstrated that most of contaminating proteins in low molecular weight calpastatin, however, did not bind to this matrix (FIG. 11). The pooled fraction was further purified over a Con A-Sepharose column. This chromatographic step was followed by heat-treatment and final gel-chromatography on Sephacryl S-300 resulted in the complete purification of the LMWC calpastatin. LMWC was purified as a single peak of activity at the position of 60 kDa protein on Sephacryl S-300 under non-denaturing condition (FIG. 2). Table 2 shows the results of purification of LMWC. The LMWC was purified 527-fold over the Ultrogel AcA44 partially purified LMWC, and the final specific activity was 19500 u/mg. FIG. 2 displays a flow diagram of the purification of low molecular weight calpastatin from human brain.

Figure 9A:
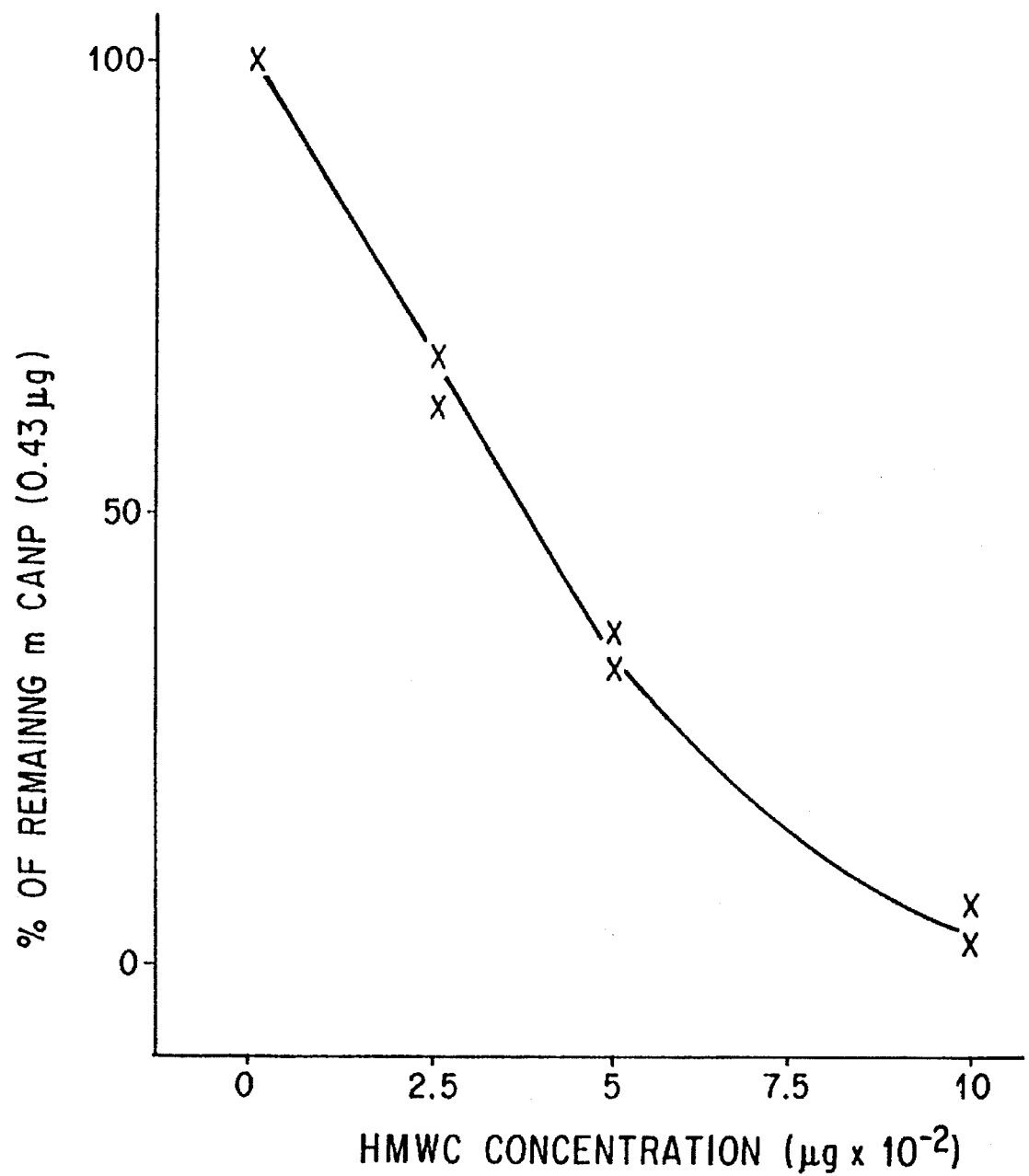
FIG. 9. Effect of varying concentrations of brain calpastatin on purified human brain mCANP. Varying amounts of purified LMWC and HMWC were incubated with 0.43 μg of purified human brain mCANP (Vitto et al., J. Neurochem. 47:1039–1051 (1986)) for 15 min under optimal conditions for CANP activity (see Examples). Relative proteolytic activity was measured as the release of TCA-soluble peptides and amino acids from $^{14}$C-azocasein (see Examples). The effects of HMWC (FIG. 9A) and LMWC (FIG. 9B) are shown.

Preliminary studies to investigate the molecular size of native low molecular weight calpastatin demonstrated that inhibitor appears to have a broad molecular distribution in its molecular weight of 40–80 kDa on Ultrogel AcA34 and 40–100 kDa on Sephadex G-200 under non-denaturing condition. This wide range of distribution of inhibitor activity suggested that low molecular weight calpastatin might be highly glycosylated as a result of posttranslational modification of this protein in vivo.

and assaying for remaining proteinase activity. The dose-dependence of the inhibitor of mCANP by HMWC is shown in FIG. 9A. The values of $ID_{50}$ (the dose of calpastatin that caused 50% inhibition) were calculated to be $0.13 \times 10^{-3}$ mM on $2 \times 10^{-3}$ mM mCANP. One molecule of 300 Kda (HMWC) calpastatin, therefore, could bind approximately 16 calpain molecules.

TABLE 2

Purification of Low Molecular Weight Calpastatin from Human Brain

| Purification Stage | Volume (ml) | Total Activity (Units)* × 10–3 | Total Protein (mg) | Yield (%) | Specific Activity (units/mg) | Purification (–fold) |
|---|---|---|---|---|---|---|
| Human Brain Homogenate | 3600 | | | | | |
| DEAE-cellulose Pooled Fraction (DE-I) | 1080 | 55.0 | 1500 | 100 | 37 | 1 |
| Ultrogel AcA 44 Fraction II (U-2) | 210 | 20.1 | 315 | 37 | 63 | 1.7 |
| CM-cellulose | 45 | 15.2 | 16.8 | 28 | 905 | 24.5 |
| Heat-treatment (100° C., 10 min) 100,000 × g Supernatant | 5 | 13.4 | 9.2 | 24 | 1457 | 39.4 |
| Sephacryl S-300 | 25 | 8.2 | 0.42 | 15 | 19523 | 527.6 |

*One unit of inhibitor activity was defined as the inhibition of 50% of the activity of 0.5 µg of CANP.

Immunoblotting and Isoelectric Focusing of Purified HMW and LMW Calpastatins

Figure 7:
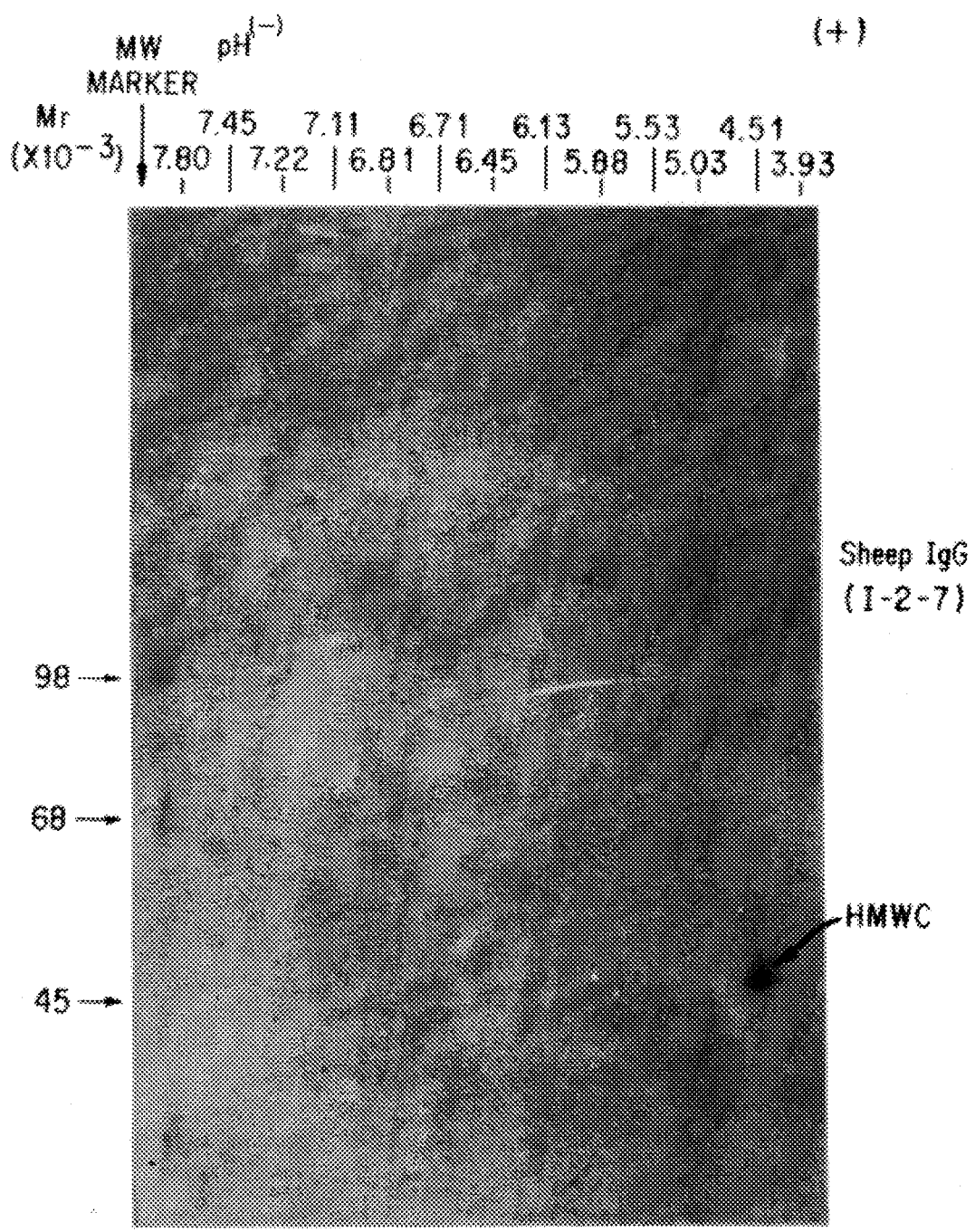
FIG. 7. Two-dimensional gel electrophoresis and immunoblotting of purified HMWC. Purified HMWC was electrophoresed on the gels containing 6.9% acrylamide, 2.5% ampholine (pH 3–8), 1.6M urea and 0.5% NP-40. After completion of 2nd-dimensional gels on SDS-PAGE (10% polyacylamide gels), proteins were electrophoretically transferred to PVDF-membrane for immuno-staining of HMWC with affinity purified I-2-7 (sheep polyclonal antibody to HMWC). The arrow indicates the position of purified HMWC at pI=4.5.
Figure 8:
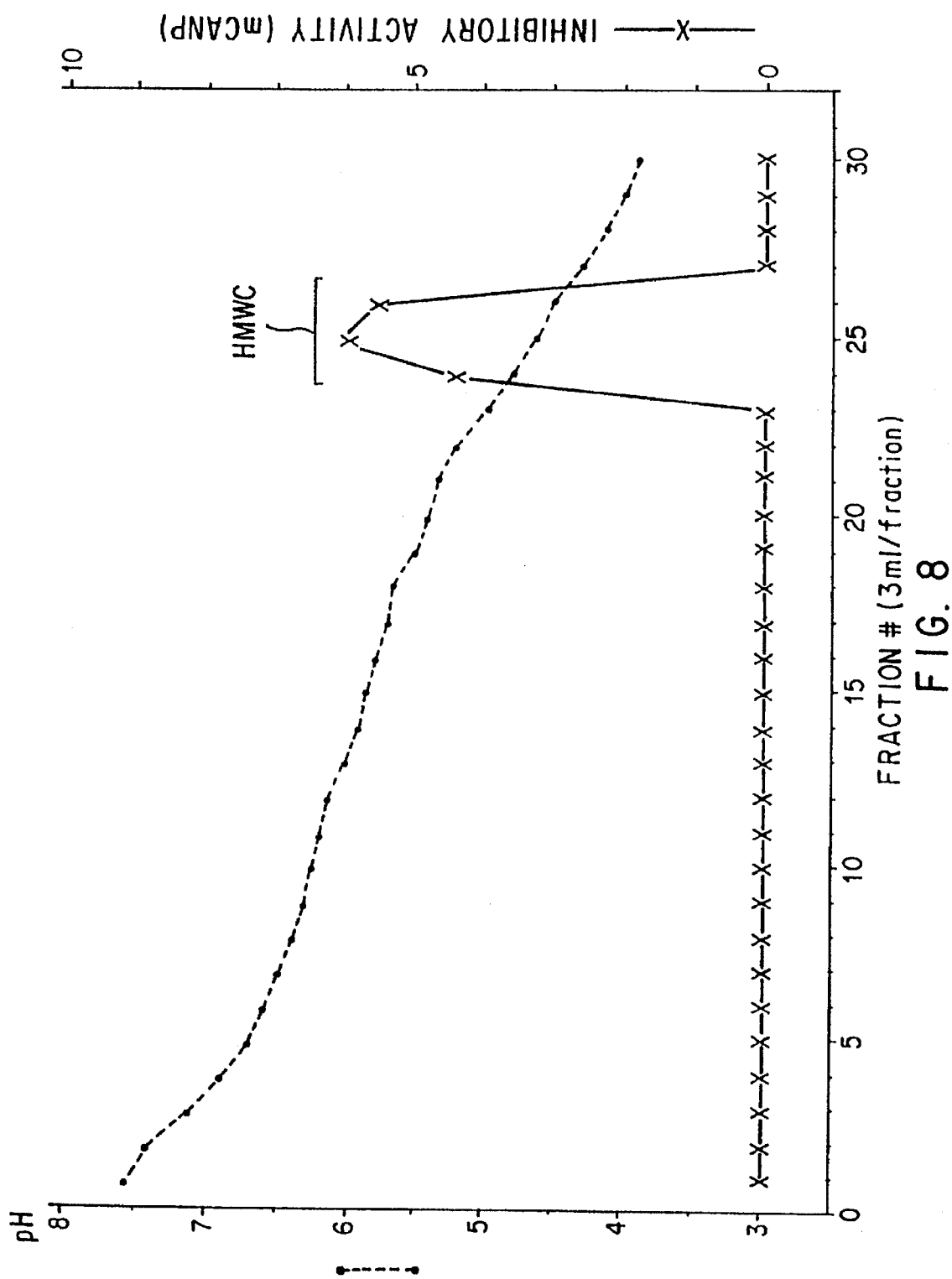
FIG. 8. Isoelectric focusing of HMWC of human brain. Purified HMWC from Ultrogel AcA34 column was electrophoresed on the polyacrylamide isoelectric focusing gels in ampholine 3–8 (pH) at 4° C. After electrophoresis, the gel was sliced into 3 mm segments. Each slice was incubated with mCANP at 0° C. for 10 hours by gentle shaking. Calpastatin activity was examined by the standard protocol. The arrow indicates the position of HMWC (at pI=4.5) on isoelectric focusing gel.

Purified HMWC was further examined by 2D-gel protein analysis followed by immunoblotting. When inhibitory activity was examined with mCANP/[$^{14}$C]-azocasein system in the extracts from isoelectric focused polyacrylamide gels (1 dimensional analysis), a single peak of inhibitory activity was demonstrated at the position of pI=4.5 (FIG. 8). Affinity-purified polyclonal antibody I-2-7 identified a single peptide having very acidic pI (pI=4.5) at 41 Kda by immunoblotting (FIG. 7).

The protein staining by silver-staining on SDS-PAGE after the two-dimensional process demonstrated a single spot which corresponded to 41 Kda immunoreactive protein on the same gels.

Figure 13:
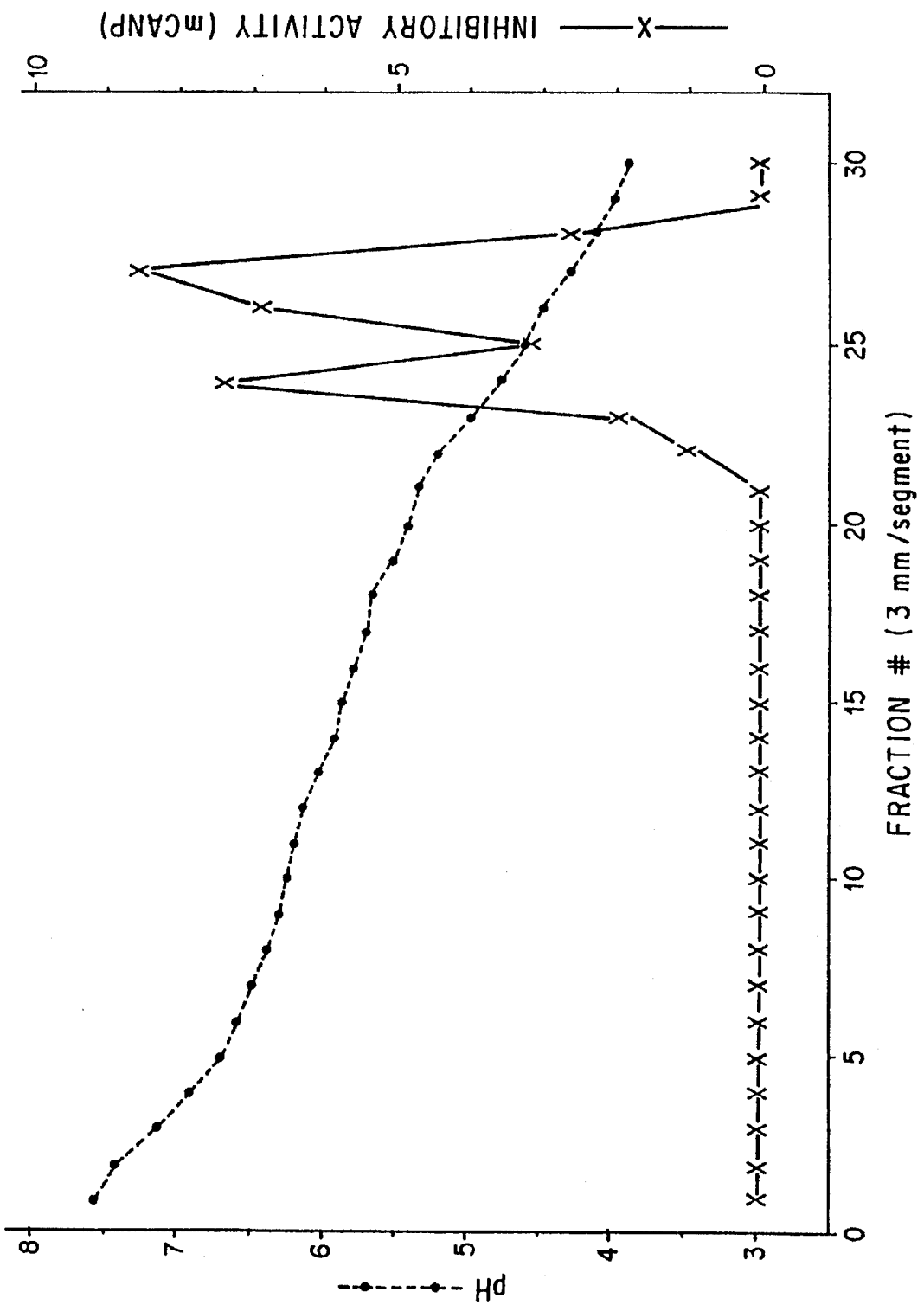
FIG. 13. Isoelectric focusing of LMWC of human brain. Purified LMWC was electrophoresed on the isoelectric focusing gels in ampholine 3–8 (pH) at 4° C. After electrophoresis, the gel was sliced into 3 mm segments for inhibitor assay. Two peaks are shown with inhibitory activity by the standard inhibitor assay protocol.

As seen in FIG. 13, purified low molecular weight calpastatin appeared as two peaks on isoelectric focusing gels. The isoelectric point of LMWC was in the range of 4.2–4.7.

Heat-stability

Since calpastatins from other sources exhibit remarkable heat stability, we examined the activity of high molecular weight and low molecular weight brain calpastatin after a 5-min exposure to a temperature of 100° C. As seen in Table 1 and 2, even after treatment at 100° C. for 5 min, the inhibitory activity was stable.

Low concentrations of purified LMW inhibitor were capable of inhibiting purified human brain mCANP. Both forms of purified human brain calpastatin (HMWC and LMWC) inhibited purified mouse brain mCANP and a micromolar calcium-dependent CANP activity in mouse retinal ganglion cell axons (Nixon et al., *J. Neurosci.* 6:1252–1263 (1986)). Neither inhibitor had effects on the activities of trypsin, chymotrypsin, bromolain, papain, and purified human brain cathepsin D, when assayed as described above.

Stoichiometry of mCANP and Calpastatin Interaction

Figure 9B:
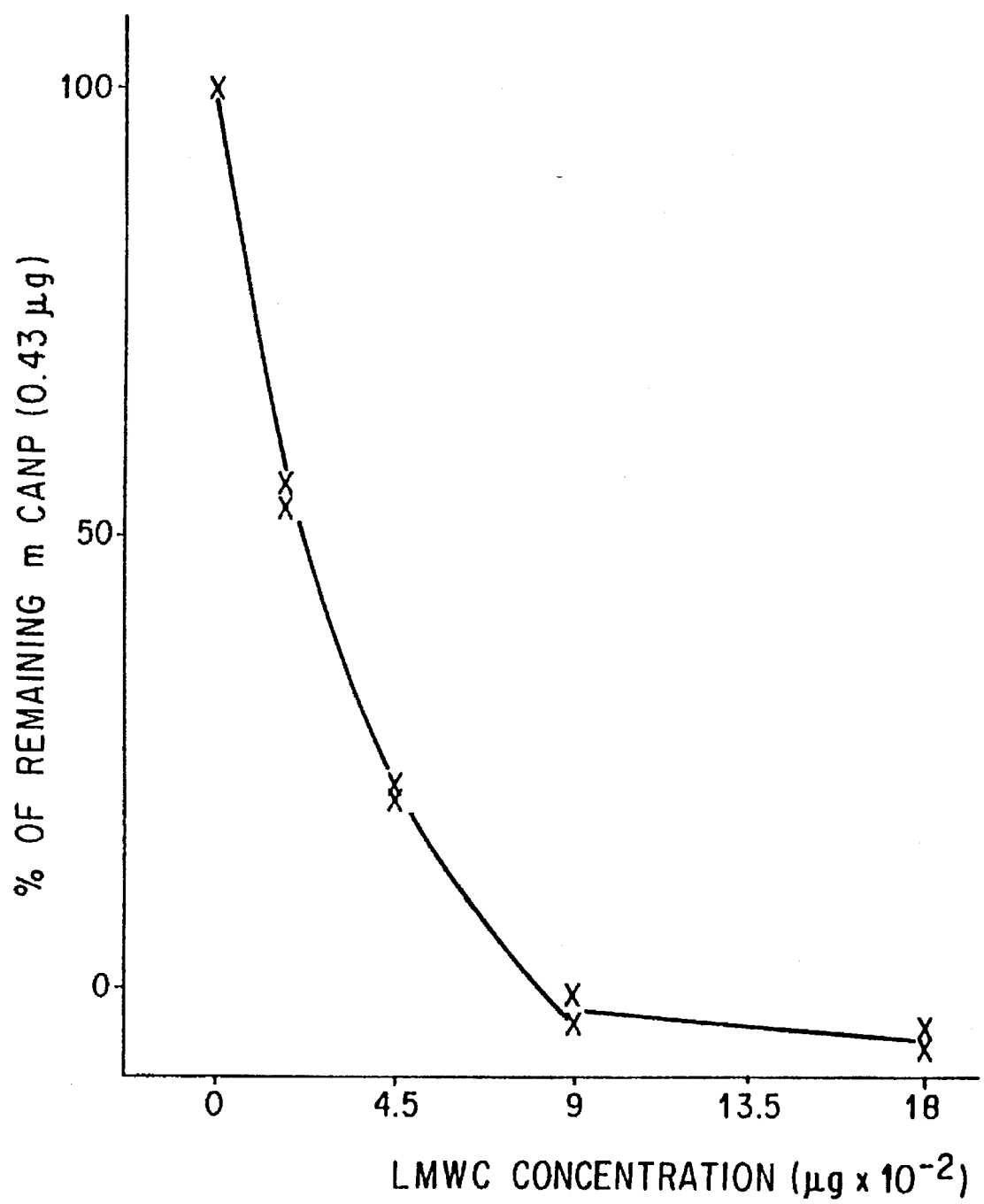
Figure 10:
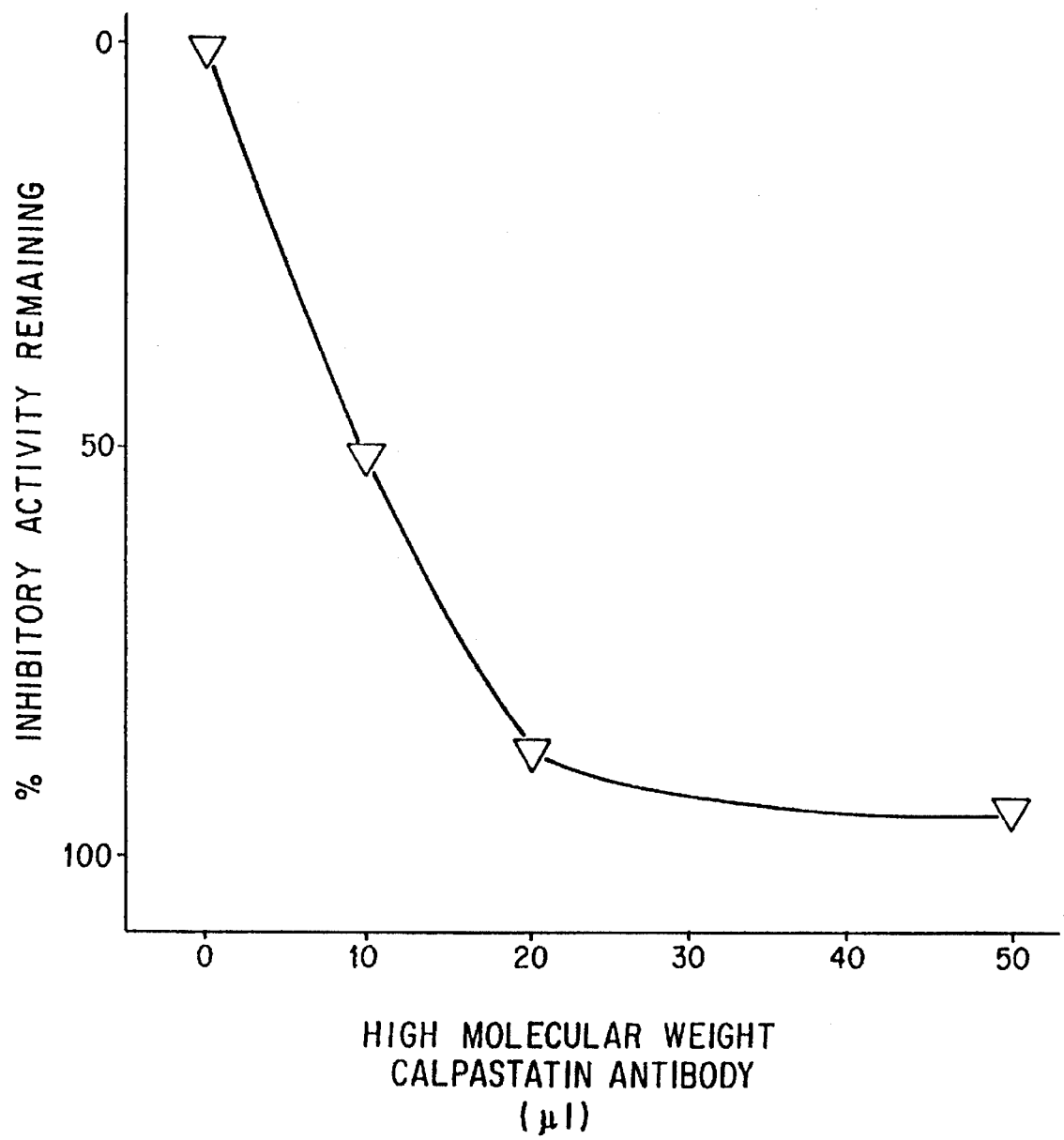
FIG. 10. Immunoprecipitate of HMWC calpastatin by I-2-7-polyclonal antibody. Ten μl of the purified HMWC was incubated with various amounts of antibody (I-2-7) raised against HMWC from human brain. IgG-HMWC complexes were removed by Protein G. Remaining supernatants were examined for inhibitor activities.

The availability of both purified mCANP and purified calpastatins made it possible to study the number of proteinase molecules inactivated by one calpastatin polypeptide simply by mixing a known ratio of mCANP and calpastatin In contrast, the $ID_{50}$ value of LMWC was $0.3 \times 10^{-3}$ mM on $2 \times 10^{-3}$ mM mCANP (FIG. 9B). The binding ratio of LMWC to mCANP is estimated to be 6 calpain molecules.

Thus, 300 kDa calpastatin has a calpain binding capacity 2.6–2.7 times that of 60 kDa calpastatin.

Amino Acid Analysis and Sequence Analysis of Calpastatin Proteins from Human Brain HMWC demonstrates a relatively high content of acidic residues, such as aspartic acid and glutamic acid, and neutral aliphatics such as glycine, alanine and serine (Table 3). The amino acid composition of HMWC was compared with the two different calpastatins, pig heart calpastatin (107 kDa protein) and rabbit liver calpastatin (68 kDa protein) (Table 4). $NH_2$-terminal sequence analysis was performed in triplicate on 25 pmole of HMWC through 19 cycles. The sequence as shown in Table 5 is as follows:

$NH_2$-X-Met-Pro-Pro-Glu-Pro-Ala-Thr-Leu-Lys-Gly-X-Val-Pro-Asp-Asp-Ala-Val-Glu (SEQ ID NO: 1)

A computer search using a protein data base (program Univ. Wisconsin genetic groups) revealed that a part of the amino acid sequence of HMWC showed some homology to other calpastatins, such as pig heart calpastatins and rabbit liver calpastatins. Although the size of these three proteins varies somewhat, the homology of the corresponding amino acid sequences between pig heart calpastatin and human brain HMWC, rabbit liver calpastatin and human brain HMWC was 36% and 34%, respectively.

Table 6 shows the amino acid composition of LMWC. Amino-terminal sequence analysis of LMWC is shown in Table 7.

An additional comparison of acid compositions was made between brain HMWC and human liver calpastatin as deduced from the complete gene sequence (Table 4A). Since the N-terminal 19 amino acids of brain HMWC corresponds precisely to an internal sequence in the cDNA of liver calpastatin, we compared the amino acid composition of brain HMWC to that of the C-terminal end of human liver calpastatin (approximately a 41-kDa polypeptide) starting at the beginning of the homologous internal sequence (Table 4A). The clear differences between this fragment of liver calpastatin and the 41-kDa HMWC indicate that the brain calpastatin is distinct from the liver calpastatin, despite regions of marked homology.

TABLE 3

Amino Acid Analysis of High Molecular Weight Calpastatin[1]

| Amino Acid | | HMWC (41 kDa)[2] mole (%) |
|---|---|---|
| Asx[3] | (D,N) | 15.1 |
| Thr | (T) | 2.5 |
| Ser | (S) | 10 |
| Glx[4] | (E,Q) | 16.7 |
| Pro | (P) | 4.7 |
| Gly | (G) | 11.1 |
| Ala | (A) | 9 |
| Cys/2 | (C) | 0 |
| Val | (V) | 3.2 |
| Met | (M) | 1.8 |
| Ile | (I) | 0 |
| Leu | (L) | 7 |
| Tyr | (Y) | 1.5 |
| Phe | (F) | 1.9 |
| Lys | (K) | 10.5 |
| His | (H) | 1.6 |
| Arg | (R) | 3.3 |
| Try | (W) | — |

[1] HMWC was purified on an Ultrogel AcA34 column as 300 kDa protein under non-denaturing conditions. Purified HMWC was subjected to SDS-PAGE and protein was transferred to the PVDF-membrane from the gel. Amino acid composition was directly determined from the membrane according to Matsudaira (J. Biol. Chem. 262, 10035, 1987).
[2] Molecular weight of HMWC was estimated on SDS-PAGE under reduced conditions.
[3] Asx = sum of aspartic acid (D) and asparagine (N).
[4] Glx = sum of glutamic acid (E) and glutamine (Q).

TABLE 4

Comparison of the amino acid composition of human brain HMWC and other $Ca^{2+}$ activated neutral proteinase inhibitors

| Amino Acid | | HMWC (41 kDa) mole (%) | Pig heart calpastatin[1] mole % | Rabbit liver calpastatin[2] mole % |
|---|---|---|---|---|
| Asx | (D,N) | 15.1 | 10.3 | 10.3 |
| Thr | (T) | 2.5 | 6.4 | 4.8 |
| Ser | (S) | 10 | 9.0 | 8.7 |
| Glx | (E,Q) | 16.7 | 14.3 | 15.7 |
| Pro | (P) | 4.7 | 11.1 | 10.2 |
| Gly | (G) | 11.1 | 6.7 | 6.5 |
| Ala | (A) | 9 | 7.6 | 12.7 |
| Cys/2 | (C) | 0 | 0.5 | 0 |
| Val | (V) | 3.2 | 5.2 | 3.3 |
| Met | (M) | 1.8 | 0.8 | 1.4 |
| Ile | (I) | 0 | 2.7 | 7.7 |
| Leu | (L) | 7 | 7.5 | 0.9 |
| Tyr | (Y) | 1.5 | 0.7 | 1.1 |
| Phe | (F) | 1.9 | 1.4 | 11.3 |
| Lys | (K) | 10.5 | 10.8 | 0.8 |
| His | (H) | 1.6 | 1.0 | 3.0 |
| Arg | (R) | 3.3 | 4.0 | — |
| Try | (W) | — | 0 | |

[1] Amino acid composition was taken from Murachi's group (Biochem. J. 235, 97, 1986).
[2] Amino acid composition was taken from Suzuki's group (Proc. Natl. Acad. Sci. 84, 3590, 1987).

TABLE 4A

Human Liver Calpastatin: deduced AA compositions

| Amino Acid | Total Sequence | 41 kDa C-terminal Fragment | 42 kDa N-terminal Fragment | Human Brain HMWC | Amino Acid |
|---|---|---|---|---|---|
| A ala | 6.6 | 6.3 | 6.8 | 9 | A ala |
| V val | 3.5 | 2.9 | 4 | 3.2 | V val |
| L leu | 7 | 7.9 | 6.4 | 7 | L leu |
| I ilu | 2 | 1.4 | 2.5 | 0 | I ilu |
| G gly | 3 | 2.9 | 3.2 | 11.1 | G gly |
| W trp | 0 | 0 | 0 | 0 | W trp |
| Y tyr | 1.3 | 1 | 1.5 | 1.5 | Y tyr |
| F phe | 1 | 1.3 | 0.7 | 1.9 | F phe |
| H his | 0.9 | 0.8 | 1 | 1.6 | H his |
| S ser | 8.5 | 7.2 | 9.6 | 10 | S ser |
| T thr | 5.3 | 5.5 | 5.1 | 2.5 | T thr |
| P pro | 8.8 | 9.1 | 8.6 | 4.7 | P pro |
| C cys | 0.9 | 0.7 | 1 | 0 | C Cys |
| M met | 1.4 | 1.2 | 1.6 | 1.8 | M met |
| R arg | 3.7 | 3.3 | 4.1 | 3.3 | R arg |
| K lys | 16.4 | 16.7 | 16.1 | 10.5 | K lys |
| E glu | 14.2 | 11.2 | 16.6 | 16.7 | E glu |
| Q gln | 3.7 | 4 | 3.4 | — | Q gln |
| D asp | 10.5 | 14.9 | 7.1 | 15.1 | D asp |
| N asn | 1.3 | 1.8 | 0.8 | — | N asn |

TABLE 5

Amino-terminal Sequence of High Molecular Weight Calpastatin of Human Brain

| 1 | 2 | 3 | 4 | 5 | 6 | 7 | 8 | 9 | 10 |
|---|---|---|---|---|---|---|---|---|---|
| X | Met | Pro | Pro | Glu | Pro | Ala | Thr | Leu | Lys |
| | M | P | P | E | P | A | T | L | K |

| 11 | 12 | 13 | 14 | 15 | 16 | 17 | 18 | 19 |
|---|---|---|---|---|---|---|---|---|
| Gly | X | Val | Pro | Asp | Asp | Ala | Val | Glu (SEQ ID NO: 1) |
| G | X | V | P | D | D | A | V | E |

Residues are numbered from the amino terminus.

TABLE 6

Amino Acid Analysis of Low Molecular Weight Calpastatin[1]

| Amino Acid | | LMWC KDa peptide mole % |
|---|---|---|
| Asx[3] | (D,N) | 8.4 |
| Thr | (T) | 3.6 |
| Ser | (S) | 10.3 |
| Glx4 | (E,Q) | 17.1 |
| Pro | (P) | 5 |
| Gly | (G) | 16.4 |
| Ala | (A) | 6.4 |
| Cys/2 | (C) | 0 |
| Val | (V) | 4.3 |
| Met | (M) | 0.9 |
| Ile | (I) | 3.3 |
| Leu | (L) | 3.1 |
| Tyr | (Y) | 2.7 |
| Phe | (F) | 7 |
| Lys | (K) | 1.3 |
| His | (H) | 4 |
| Arg | (R) | — |
| Try | (W) | |

[1] LMWC was purified on a Sephacryl S-300 column under non-denaturing conditions. The LMWC peptide was identified on SDS-PAGE. The peptide was transferred to the PVDF-membrane from the gels. Amino acid composition of the peptide on the PVDF-membrane was determined by the methods of Matsudaira (J. Biol. Chem. 262, 10035, 1987).

TABLE 6-continued

Amino Acid Analysis of Low Molecular Weight Calpastatin[1]

| Amino Acid | LMWC KDa peptide mole % |
|---|---|

[2] Expressed as residues/100 residues.
[3] Asx = sum of aspartic acid (D) and asparagine (N).
[4] Glx = sum of glutamic acid (E) and glutamine (Q).

TABLE 7

N-Terminal Amino Acid Sequence of Low Molecular Weight Calpastatins of Human Brain

|  | 1 | 2 | 3 | 4 | 5 | 6 | 7 | 8 | 9 | 10 |
|---|---|---|---|---|---|---|---|---|---|---|
| LMWC (31 kDa) | X | E | K | E | T | K | E | E | G | K |
|  | X | Glu | Lys | Glu | Thr | Lys | Glu | Glu | Gly | Lys |
|  | 11 | 12 | 13 | 14 | 15 | 16 | 17 | 18 | 19 | 20 |
| LMWC (31 kDa) | P | L | Q | Q | Q | X | X | K | E | K |
|  | Pro | Lys | Gln | Gln | Gln | X | X | Lys | Glu | Lys |

(SEQ ID NO: 2)

V. Antibodies to HMW and LMW Calpastatin

Antibody Production

Pure samples of the LMW inhibitor are purified on a two-dimensional SDS polyacrylamide gel and are excised from the gel. The slices are equilibrated to pH 6.8 in 125 mM Tris buffer containing 0.1% SDS, are mixed with an equal amount of complete Freund's adjuvant, and are injected subcutaneously and intradermally into a female rabbit as described by Vitto et al., *J. Neurochem.* 47:1039–1051, 1986. Injections of 50 mg of protein in 2 ml of emulsion are given in monthly intervals, using complete Freund's adjuvant initially, and incomplete Freund's adjuvant in subsequent injections. Animals are bled 7–10 days after injection. The blood is allowed to clot and is spun to obtain serum (Vitto et al., *J. Neurochem.* 47:1039–1051, 1986). Additional antibodies are prepared by immunizing sheep with gel slices containing the purified polypeptide using the same procedure described above for rabbit except that 50–100 mg of protein are used for each immunization.

Antibodies to HMWC were prepared in sheep by injecting the purified 41-kDa polypeptide electrophoretically separated on 5–15% SDS-polyacrylamide gels. Antibodies against HMWC were generated and characterized. I-2 is a sheep anti-serum raised against a partially purified 41-kDa polypeptide of HMWC. Antibody specific for the purified 41-kDa HMWC was prepared by antigen affinity chromatography. Purified preparations of HMWC were electrophoretically separated and electrotransferred to PVDF membranes. Regions of the membrane containing the 41-kDa HMWC were cut into strips (antigen strips). Antigen strips were incubated for 1 hour at room temperature with 5% non-fat dry milk solution containing 2 mM EGTA, 0.15M NaCl in 50 mM Tris-HCl pH 7.4 (blocking buffer). Strips were incubated with I-2 antiserum for 1 hour at room temperature and then washed 3 times in TBS at room temperature (RT) for 5 minutes. Bound antibody was eluted from the antigen strips by incubation with 1.5 ml 0.1M glycine-HCl pH 3.0 for 10 minutes at room temperature which was immediately neutralized with 40 µL of of 1M Tris pH 11.0. Antibody solutions were concentrated using Centriprep 10 filtration units (Amicon Corp.) and stored at −70° C.

In some experiments, a second affinity purified antibody was prepared from I-2 using as the ligand the 87-kDa protein band present on gels of purified HMWC in low levels relative to 41-kDa HMWC. I-2 affinity purified antibodies to either the 41-kDa or 87-kDa protein recognized both the 41-kDa and the 87-kDa proteins although the 87-kDa antibody yielded a somewhat stronger signal with the 87-kDa antigen compared to the 41-kDa antigen. Studies detailed below involve the use of the affinity-purified I-2 antibodies (designated I-2 (41) or I-2 (87)) unless otherwise indicated.

Immunoblot Analysis

Immunoblot analysis using I-2 affinity purified antiserum demonstrated strong immunostaining of the protein band corresponding to HMWC throughout its purification. Immunoreactivity in different fractions of each chromatography step correlated well with the relative inhibitory activity of these fractions. Partially purified fractions of LMWC reacted strongly with rabbit antiserum to LMWC (I-1) but were not immunostained by the antiserum to HMWC (I-2). Conversely, a partially purified fraction of HMWC reacted with I-2 but not I-1. These results indicate the unrelatedness of HMWC and LMWC by immunologic criteria, confirming biochemical data described above.

Partially purified fractions of calpastatin were prepared from supernatant extracts of various neural and non-neural tissues by ion exchange chromatography on DEAE cellulose (step 1 of the calpastatin purification scheme). The fractions containing CANP inhibitory activity were eluted at 0.15M KCl and tested by immunoblot analysis. In some cases, the preparations were further enriched by heat treatment at 100° C. for 10 minutes to remove heat unstable proteins, which precipitated and were eliminated by centrifugation. The I-2 (41) antisera recognized strongly cross-reactive bands in the inhibitory fractions which varied in molecular weight for each tissue.

In brain samples from rabbit, monkey and human, I-2 (41) recognized a 41-kDa protein as a major immunoreactive constituent. In addition, I-2 (41) also strongly labeled a 68-kDa protein in human erythrocytes corresponding to the molecular mass of the known calpastatin in this tissue and a 50- to 55-kDa protein of unknown relation to calpastatin. In rat heart and liver, a 100- to 105-kDa immunoreactive protein was observed, which may correspond to the larger calpastatin forms previously reported in some non-neural tissue including liver. These results demonstrate the widespread occurrence of proteins immunologically related to the brain HMWC in non-neural tissues. They also demonstrate that a 41-kDa calpastatin is the major immunoreactive form of HMWC in brains from various mammalian species. This indicates that the 41-kDa form of brain HMWC is not an artifact of postmortem processing since rabbit and monkey brain was snap frozen within 20 minutes of death, comparable to the post-mortem interval for the non-neural tissue samples.

It should be noted that in highly purified fractions of human HMWC, I-2 (41) and especially I-2 (87) also recognize three minor protein bands at 87, 65 and 55 kDa. Only the 87-kDa form (and 41-kDa form) can be detected on Coomassie stained gels. We suspect that these forms may be proforms of the 41-kDa HMWC.

VI. Postmortem Stability of Calpastatins in Bovine Brain

The presence and content of polypeptides immunoreactive against antibodies to LMWC and HMWC was measured in samples of adult bovine cerebral cortex. Changes in the content of LMWC and HMWC in bovine brain were analyzed in samples of cerebral cortex dissected from calf brain removed with 10 minutes after death and maintained for various intervals at room temperature.

The results demonstrate the remarkable stability of HMWC and LMWC in postmortem tissue. During a 30-hour postmortem interval at room temperature, there was less than 10% reduction in the content of the 41-kDa component of HMWC and the 26–30 kDa components of LMWC.

VII. Immunocytochemical Studies with Affinity Purified Antisera Raised Against Calpastatin Polypeptide: Detection of Abnormalities in Alzheimer's Disease Brain Immunocytochemical findings using affinity purified antibodies to HMWC provide evidence supporting the involvement of CANP systems in AD pathogenesis. I-2 (41) and 1-2 (87) yielded identical immunocytochemical staining patterns in all brain regions of Alzheimer and control tissue as well as in mouse brain and monkey. In vibratome sections of neocortex from each of these species, immunoreactivity to HMWC was predominantly localized in neuronal perikarya and apical dendrites. Immunoreactivity was particularly abundant in large pyramidal cells of the neocortex and hippocampus. Punctate staining of dendritic arborizations in the molecular layer of the neocortex suggested additional immunolabeling of synapses. Axons and glial cells including reactive astrocytes were relatively weakly stained.

Affinity purified antibodies to the HMWC I-2 (41) or I-2 (87), detected striking abnormalities in the distribution of this antigen in neocortical and hippocampal neurons in Alzheimer's disease (AD). In comparison to control cases where dendrites of pyramidal cells in layers III and V were darkly stained and could be traced long distances toward the pial surface, levels of immunoreactivity in dendrites of the same neurons in Alzheimer's disease were markedly decreased. Perikarya of neurons in layer III also displayed reduced levels of calpastatin imunoreactivity. By contrast, immunoreactivity in deeper layers of the cortex (IV–VI) was relatively well preserved in AD brains. This distribution pattern therefore resulted in a band of dark immunostaining in layers IV–VI of Alzheimer tissue that could be differentiated from the uniform immunostaining of layers I–VI in control brains. These differences between control and Alzheimer patterns could be seen without the aid of a microscope in many cases. A survey of 12 Alzheimer and 10 control brains documented the reproducibility of these differences and demonstrated that the Alzheimer pattern of immunoreactivity appears to be present in the majority of AD brains that were suitable for immunocytochemistry. The abnormality was widespread in sections of prefrontal cortex sections and appeared to affect the dendrites of most neurons with arborizations projecting through layers I–III. In the hippocampus, similar reductions in the level of immunoreactivity to calpastatin were also observed in AD brains. No changes were detected in the cerebellum. In a series of 10 brains of individuals with Down's syndrome (age 31–70), a pattern similar to that in Alzheimer brains was seen in the majority of cases.

VIII. SUMMARY

These findings provide evidence for a potential role of calpastatins in the pathogenesis of AD. Reduced levels of calpastatin in dendrites would provide an explanation for observed abnormal activation of calpains in Alzheimer brains. These changes would be expected to contribute to and/or mediate the synaptic dysfunction and degeneration of neurons and their processes in Alzheimer's disease. The immunocytochemical patterns seen in Alzheimer and Down's brains were distinct from other histopathological markers of the disease process (e.g., senile plaques and neurofibrillary tangles) and may therefore represent a useful diagnostic marker for Alzheimer's disease. Furthermore, restoration of calpastatin levels in neurons, or the pharmacologic equivalent, may prove to be a means for reducing the rate of neuronal degeneration and degree of synaptic dysfunction in Alzheimer's disease and thereby may be an effective treatment strategy in this disease.

Modifications of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An antibody specifically immunoreactive with an immunogen, wherein said immunogen consists essentially of a substantially purified, low molecular weight calpastatin with a molecular weight of about 60 kilodaltons, as determined by gel filtration, and consisting of a dimer of about 31 kilodalton subunits, as determined by SDS PAGE under reducing conditions, and wherein said calpastatin has a pI range of 4.2–4.7 on an isoelectric focusing gel and an N-terminal amino acid sequence as follows:

$NH_2$-X-Glu-Lys-Glu-Thr-Lys-Glu-Glu-Gly-Lys-Pro-Lys-Gln-Gln-Gln-X-X-Lys-Glu-Lys (SEQ ID NO: 2)

wherein X represents an unknown amino acid residue; wherein said calpastatin has the following amino acid composition:

| | Mole % |
|---|---|
| Asx | 8.4 |
| Thr | 3.6 |
| Ser | 10.3 |
| Glx | 17.1 |
| Pro | 5 |
| Gly | 16.4 |
| Ala | 6.4 |
| Cys/2 | 0 |
| Val | 4.3 |
| Met | 0.9 |
| Ile | 3.3 |
| Leu | 3.1 |
| Tyr | 2.7 |
| Phe | 7 |
| Lys | 1.3 |
| His | 4 | wherein:

Asx=sum of aspartic acid (D) and asparagine (N), and

Glx=sum of glutamic acid (E) and glutamine (Q);

and wherein said calpastatin is capable of inhibiting calcium-activated neutral proteinase activity.

2. A method of detecting pathological structures in the neurons of patients suffering from Alzheimer's Disease and related neurofibrillary disorders, or neurodegenerative states characterized by cell degeneration and cell death which comprises immunocytochemically staining said pathological structures with an antibody of claim 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 19 amino acids
( B ) TYPE: amino acid
( D ) TOPOLOGY: both ( x i ) SEQUENCE DESCRIPTION: SEQ ID NO:1:

Xaa Met Pro Pro Glu Pro Ala Thr Leu Lys Gly Xaa Val Pro Asp Asp
1               5                   10                  15

Ala Val Glu ( 2 ) INFORMATION FOR SEQ ID NO:2:

( i ) SEQUENCE CHARACTERISTICS:
  ( A ) LENGTH: 20 amino acids
  ( B ) TYPE: amino acid
  ( D ) TOPOLOGY: both ( x i ) SEQUENCE DESCRIPTION: SEQ ID NO:2:

```
Xaa Glu Lys Glu Thr Lys Glu Glu Gly Lys Pro Lys Gln Gln Gln Xaa
1               5                   10                  15
Xaa Lys Glu Lys
            20
```